United States Patent
Schussler

(10) Patent No.: US 11,154,289 B2
(45) Date of Patent: Oct. 26, 2021

(54) BONE DISTRACTOR

(71) Applicant: Buxton BioMedical, Inc., East Hanover, NJ (US)

(72) Inventor: Annie M. Schussler, Denville, NJ (US)

(73) Assignee: Buxton Biomedical, Inc., East Hanover, NJ (US)

(*) Notice: Subject to any disclaimer, the term of this patent is extended or adjusted under 35 U.S.C. 154(b) by 116 days.

(21) Appl. No.: 16/530,261

(22) Filed: Aug. 2, 2019

(65) Prior Publication Data

US 2020/0060666 A1 Feb. 27, 2020

Related U.S. Application Data

(60) Provisional application No. 62/722,777, filed on Aug. 24, 2018.

(51) Int. Cl.
*A61B 17/02* (2006.01)

(52) U.S. Cl.
CPC ........ *A61B 17/025* (2013.01); *A61B 17/0206* (2013.01)

(58) Field of Classification Search
CPC ... A61B 17/02; A61B 17/0206; A61B 17/025; A61B 2017/0256; A61B 2017/0262; A61B 2017/0268; A61B 2017/0275
See application file for complete search history.

(56) References Cited

U.S. PATENT DOCUMENTS

| | | | | |
|---|---|---|---|---|
| 3,470,872 A | * | 10/1969 | Grieshaber | A61B 17/0206 600/217 |
| 6,565,570 B2 | * | 5/2003 | Sterett | A61B 17/025 606/280 |
| 8,092,488 B2 | * | 1/2012 | DiNucci | A61B 17/025 606/205 |
| 9,237,899 B2 | * | 1/2016 | Ray | A61B 17/062 |
| 9,610,072 B2 | * | 4/2017 | Assia | A61B 17/0231 |
| 9,808,272 B2 | * | 11/2017 | Wohl | A61B 17/24 |
| 9,999,414 B2 | * | 6/2018 | Ruppert | A61B 17/0206 |
| 10,123,832 B2 | * | 11/2018 | Knoepfle | A61B 17/82 |
| 2005/0215864 A1 | * | 9/2005 | Jang | A61B 17/0206 600/217 |
| 2007/0299315 A1 | * | 12/2007 | Geller | A61B 17/0206 600/217 |
| 2010/0022845 A1 | * | 1/2010 | Ott | A61B 17/0206 600/215 |
| 2012/0130180 A1 | * | 5/2012 | Pell | A61B 17/025 600/206 |
| 2014/0288380 A1 | * | 9/2014 | Assia | A61B 50/30 600/236 |
| 2015/0065809 A1 | * | 3/2015 | Assia | A61B 17/0231 600/217 |
| 2016/0038200 A1 | * | 2/2016 | Knoepfle | A61B 17/82 606/324 |
| 2020/0060666 A1 | * | 2/2020 | Schussler | A61B 17/0206 |

* cited by examiner

*Primary Examiner* — Eric S Gibson
(74) *Attorney, Agent, or Firm* — Neil D. Gershon

(57) ABSTRACT

A bone distractor having first and second prongs each having a side having a serrated portion and an opposing side having a portion smoother than the serrated portion. In an insertion position, the serrated sides are positioned inwardly so the smoother portions are in contact with bone during insertion. During a use position to distract bone, the serrated sides are moved outwardly to place the serrated portions in contact with bone.

17 Claims, 27 Drawing Sheets

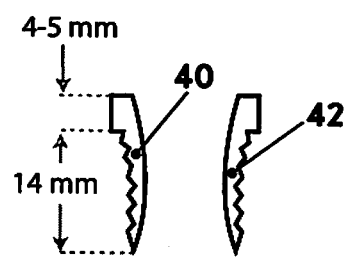
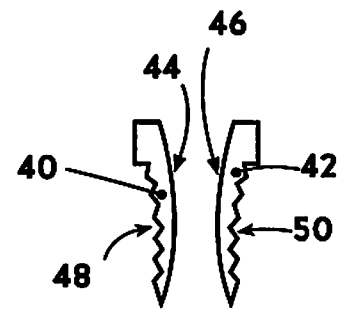
Figure 9A  Figure 9B
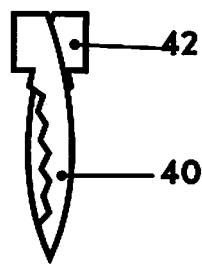
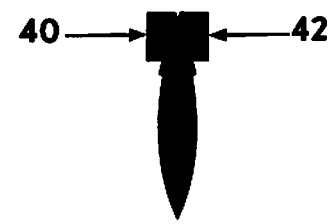
Figure 9C  Figure 9D
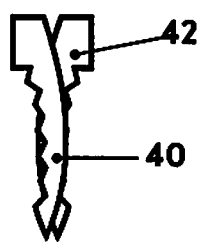
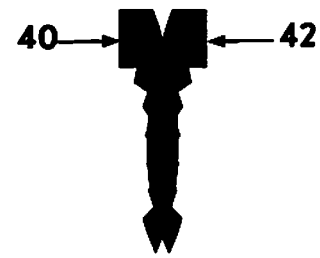
Figure 9E  Figure 9F

BONE DISTRACTOR

This application claims priority from provisional application 62/722,777, filed Aug. 24, 2018, the entire contents of which are incorporated herein by reference.

BACKGROUND

Technical Field

This application relates to a bone distractor and more particularly to a bone distractor for sliding into tight joints in the human body.

Background of Related Art

There are two main types of bone distractors (also referred to as spreaders). The first type is the extra-articular distractor which features guides for pins and screws into the bones to be distracted. The other type of bone distractor is the intra-articular distractor which is inserted between the surfaces of the joint and then distracts. A very popular form of these distractors is standard Lamina Spreaders which are illustrated in FIG. 1 and are designed for spine surgery. The Lamina Spreader is designed to fit between two vertebrae that have thick disc material between them which can be scraped away to allow insertion. The "paddles" of lamina spreaders are often five or more millimeters thick with serrations or teeth that will hold well against the bone when in the distracted position, but require at least 5 mm of joint clearance to achieve insertion.

For use in joints such as those in the ankle, the bones do not have the thick cushioning that vertebral bones have and the ligaments that hold them together are very strong. Therefore, getting 5 mm clearance between these bones requires a bit of levering, scraping and cutting to fit this distractor into the joint space. Once in the joint space, the distractor is not likely to budge, which is why, despite the difficulty and time it takes to insert, the lamina spreader takes a prominent position in the foot surgeon's instrument set. However, it is basically too thick to fit between tight joint spaces Another current small bone spreader is illustrated in FIG. 2 and is sold by Buxton BioMedical, Inc. as the "Small Bone Spreader." The spreader is wedge shaped and, with a little skill, is able to slide into tight joints. The tip of the spreader is constructed with one half of the wedge on one side and the other half of the wedge on the other side. These two half wedges meet at the medial plane in the closed position. However, there is a drawback with this spreader since once it opens and distracts, it is unstable. Unless someone is there to hold it open, the distractor can easily twist or slip out. This is because the paddles of the spreader are mostly smooth with barely a hint of a "serration." Although it is designed for insertion into tight joints, it cannot really achieve sustained hand-free distraction. Thus, although it might provide smooth entry, it has poor retention.

It is recognized that to access tight spaces, thinner spreader paddles would be beneficial, however, limitations in material strength and resilience restrict this approach as a sole or satisfactory solution. That is, strength of the paddles would be sacrificed if they are too thin which would make it ineffective for spreading bone. Furthermore, such thinner paddles would not help solve the problem of dislodgement and if not held by a clinician, could slip out. Still further, if serrations are added to the thinner paddles to try to better hold it in place, it would gum up insertion, thereby making insertion more difficult.

The wedge shape of the Buxton Small Bone Spreader accomplishes the task of smooth entry and the narrow tip of the wedge might provide the requisite "thinness", but it quickly thickens into something substantial that must withstand pressures of the joint. Another approach to "thinness" is provided by another type of lamina spreader, illustrated in FIG. 3, and sold by Buxton Biomedical, Inc. as the "Buxton Lamina Spreader, Bayonet." This spreader (distractor) is a "1×2" inter-digitated spinal distractor that provides a low profile. The distractor has a swan neck "bayonet" shaft and blunt tips. The "paddle" sides of the interdigitated instrument incorporate widely spaced prongs instead of solid "blades." The prongs are straight and the serrations are minimal. Much like fingers in clasped hands, it allows for the prongs of one side of the instrument to sit alongside or pass through the prongs of the other side of the instrument. Instead of having one plane where the two sides meet as in the small bone spreader of FIG. 2, each prong crosses this plane. This is common in soft tissue retractors such as Weitlaner retractors (see e.g., FIG. 4 where the prongs spread when the handles are squeezed together) and allows for a lower profile especially when there are lateral prongs that need to enter a small space. The interlacing of these prongs not only provides a low profile, but also allows for each prong to be substantially thicker and therefore stronger than two thin solid paddles entering the same space. In a way, it allows the two sides of the distracting paddles to occupy, essentially, the "same space." However, for spinal distraction, this distractor suffers the same problems as the aforementioned wedge Small Bone Spreader and bayonetted Buxton Lamina Spreader, as although it can fit into a small space, it cannot hold (remain in the space) very effectively. There are 2-3 slight peaks than give a nod to a serration, but nothing substantial that will impede smooth insertion and therefore nothing that will substantially hold onto the distracted joint without assistance.

The need exists for a distractor that maintains its integrity while performing all required tasks: insertion, distraction, unassisted retention, and removal. To date, no distractor achieves all these objectives. Current distractors, might achieve one or more objectives, but at the cost of sacrificing achievement of other objectives. Therefore, current distractors cannot effectively slide into tight joints to distract the bone, remain in position and be easily removed after the procedure.

SUMMARY

The present invention overcomes the problems and deficiencies of the prior art. The present invention provides a bone distractor with serrated surfaces shielded for entry into the bone and exposed for bone distraction. The configuration of the prongs further facilitates insertion, distraction, securement and removal. One or both of the distractor arms can be retained in a select position to retain the desired position of the prongs. Various embodiments of the distractors are disclosed herein.

In accordance with one aspect of the present invention, a bone distractor is provided comprising a) a first prong having a first side having a serrated portion and a second side having a portion smoother than the serrated portion; and b) a second prong having a third side having a serrated portion and the fourth side having a portion smoother than the serrated portion. In an insertion position of the bone distractor, the first side is positioned inwardly of the fourth side and the third side is positioned inwardly of the second side so the smoother portions are in contact with bone during insertion. During a use position of the bone distractor to distract bone, the first side is moved outwardly of the fourth side and the third side is moved outwardly of the second side to place the serrated portions in contact with bone.

In some embodiments, the first and second prongs interdigitate. The first prong can have two serrated portions forming a space therebetween, and in the insertion position the second prong is positionable within the space.

In some embodiments, the bone distractor has a longitudinal axis, and the serrated portions of the first and third sides comprise a series of teeth in a row extending transverse to the longitudinal axis.

In some embodiments, the first and third sides are concave; in other embodiments, the first and third sides are convex. In some embodiments, the second and fourth sides are convex.

In some embodiments, the tip of the first and second prongs form a half wedge; in other embodiments, the first and second prongs have a full wedge tip forming a ledge at an entry point.

In accordance with another aspect of the present invention, a bone distractor is provided comprising a first prong extending from a first arm and a second prong extending from a second arm. The first and second prongs are movable between open and closed positions. The first and second prongs each having a serrated side, wherein in the closed position for insertion into a bone space, the serrated sides of the first and second prongs are out of engagement with the bone and movement of the prongs to the open position moves the serrated sides of the first and second prongs into engagement with the bone.

In some embodiments, the first and second prongs each have a smoother side opposite the serrated side, and in the closed position the serrated side of the first prong is positioned inwardly of the smoother side of the second prong and the serrated side of the second prong is positioned inwardly of the smoother side of the first prong so that the serrated sides are kept out of contact with the bone for insertion.

In some embodiments, the non-serrated sides are concave. In some embodiments, movement of the first and second prongs to the open position to distract the bone moves the serrated sides of the first and second prongs past the medial plane. In some embodiments, in the closed position, the first and second prongs interdigitate.

In accordance with another aspect of the present invention, a method of distracting bone is provided comprising:
a) inserting a bone distractor having a first prong and a second prong in a closed position such that a serrated side of the first and second prongs are shielded from contact with the bone;
b) opening the bone distractor to move the serrated sides of the first and second prongs into contact with the bone to distract the bone; and
c) subsequently returning the first and second prongs to the closed position and removing the first and second prongs while shielded from contact with the bone.

In some embodiments, movement of the first and second prongs to distract the bone moves the serrated sides of the first and second prongs past the medial plane.

In some embodiments, the first prong has two serrated portions forming a space therebetween, and in the insertion position the second prong is positionable within the space.

BRIEF DESCRIPTION OF THE DRAWINGS

Preferred embodiment(s) of the present disclosure are described herein with reference to the drawings wherein:

FIG. 9A-9L illustrate an alternate embodiment of the distractor of the present invention wherein:

FIG. 9A is a front view of the prongs of the distractor in a fully open position;

FIG. 9B is a front view of the prongs of the distractor in a partially open position;

FIG. 9C is a front view of the prongs of the distractor in a closed position;

FIG. 9D is a schematic front view showing the smooth wedge shape of the two closed prongs corresponding to the position of FIG. 9C;

FIG. 9E is a front view of the prongs in transition between the closed insertion position and the spread position;

FIG. 9F is a schematic front view showing the narrowest profile of the prongs during transition corresponding to the position of FIG. 9E;

FIG. 9G is a perspective view of the distractor showing the prongs in the closed position;

FIG. 9H is a perspective view of the distractor showing the prongs in a partially open position;

FIG. 9I is a perspective view of the distractor showing the prongs in the a more fully open position;

FIG. 9J is a side perspective view of the prongs of the distractor in a closed position;

FIG. 9K is a side perspective view of the prongs of the distractor in a closed position;

FIG. 9L is a top view of the prongs of the distractor in a closed position;

DESCRIPTION OF PREFERRED EMBODIMENTS

The intra-articular bone distractor (also referred to as a bone spreader) of the present invention is designed to easily slide between tight joints in the human body such as, but not limited to, the subtalar joint in the ankle, and effectively distract the bones allowing the surgeon access to this distracted space without the distractor dislodging or popping out. The distractor can be used in the subtalar joint, the tibiotalar joint, the calcaneocuboid joint and other tight joints or other regions of a patient's body where bone distraction is desired.

The bone distractor of the present invention satisfies the deficiencies of the prior art by providing an instrument that maintains its integrity while performing all required tasks: insertion, distraction, unassisted retention, removal. Thus, it can effectively slide into tights joints to distract the bone, remain in position during bone distraction and be easily removed after the procedure.

Figure 1:
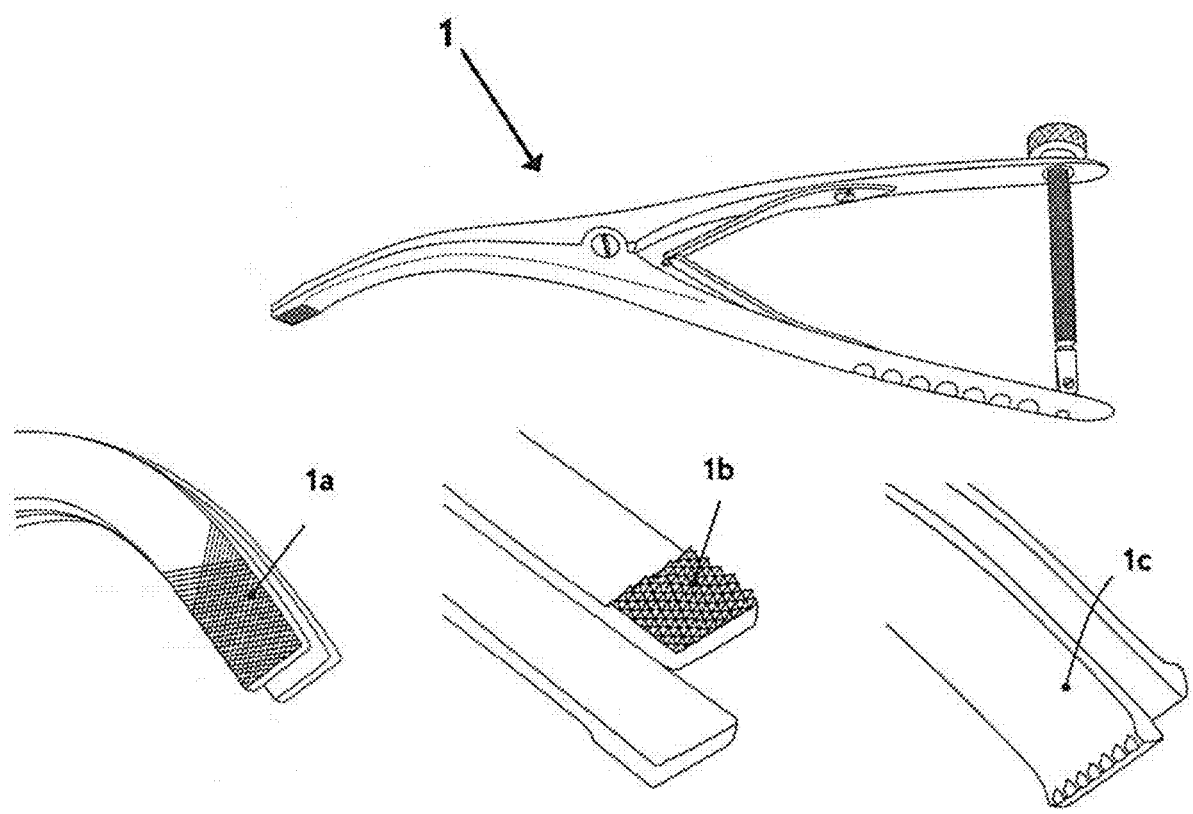
FIG. 1 illustrates a prior art intra-articular Lamina Spreader showing various tips.

Prior art bone distractors are illustrated in FIGS. 1-4. FIG. 1 shows a standard prior art lamina spreader designed for spine surgery. The Lamina Spreader 1 is designed to fit between two vertebrae that have thick disc material between them which can be scraped away to allow insertion. The "paddles" are five or more millimeters thick with serrations or teeth that will hold well against the bone when in the distracted position, but requires at least 5 mm of joint clearance to achieve insertion so cannot fit within tight joint spaces. Different paddle configurations/surfaces 1a, 1b and 1c are illustrated.

Figure 2:
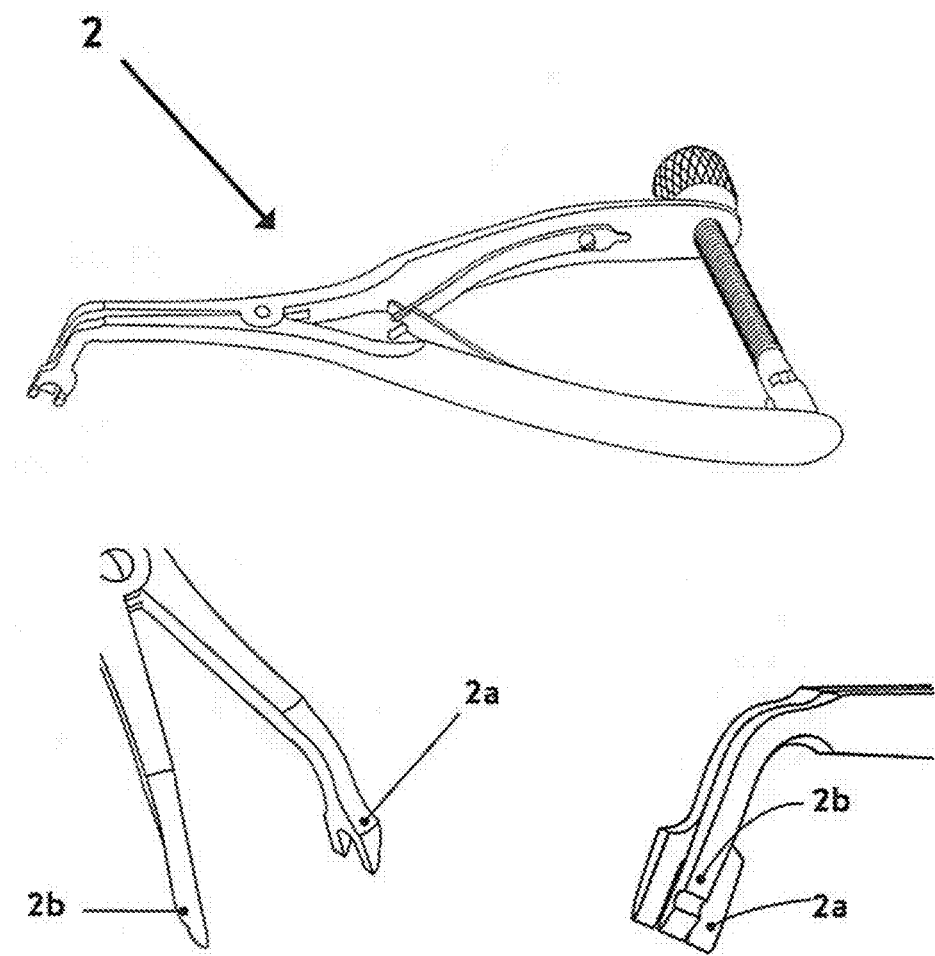
FIG. 2 illustrates a prior art intra-articular Small Bone Spreader.

Another prior art small bone spreader 2 is illustrated in FIG. 2 having a wedge-shape for sliding into tight joints. The tip of the spreader is constructed with one half of the wedge on one side and the other half of the wedge on the other side. These two half wedges meet at the medial plane in the closed position. The paddles 2a of the spreader are mostly smooth. The spreader (distractor) is held open to prevent it from twisting or slipping out.

Figure 3:
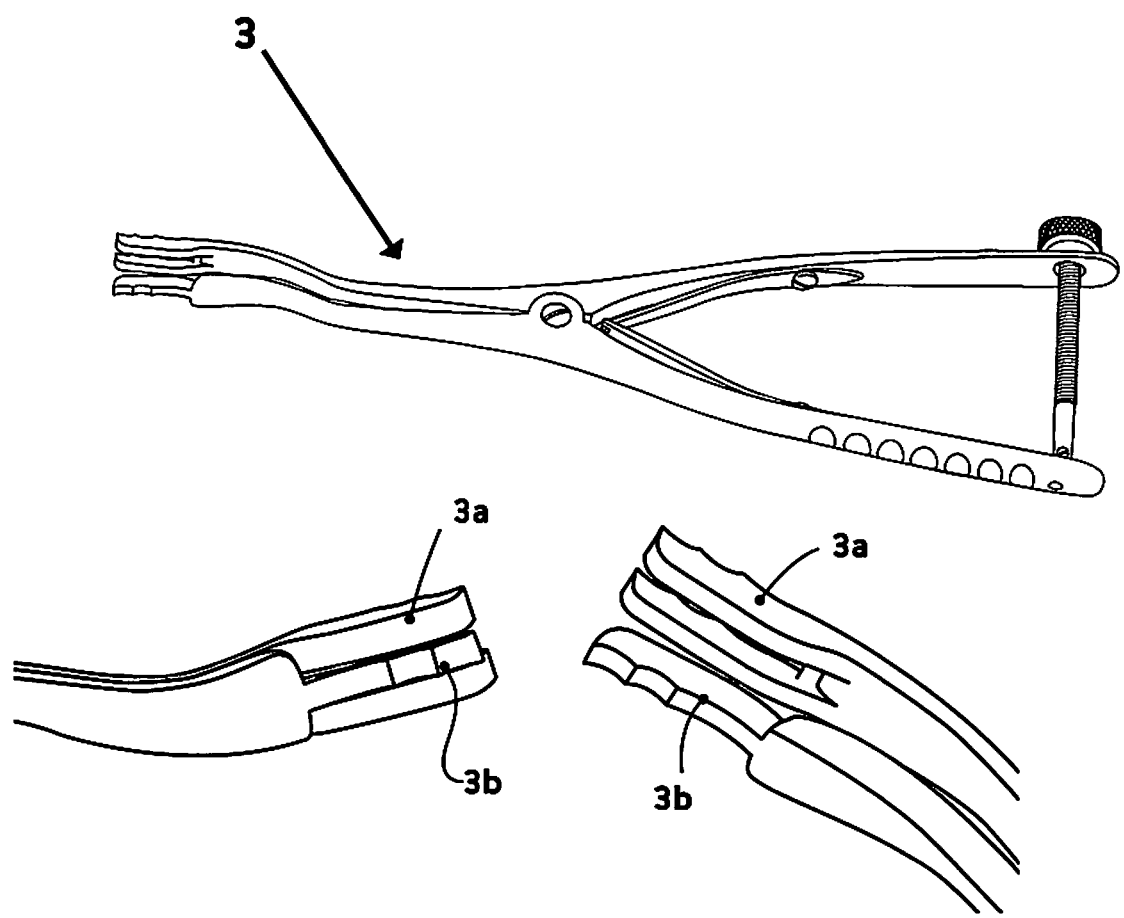
FIG. 3 illustrates a prior art bayoneted Lamina Spreader.
Figure 4B:
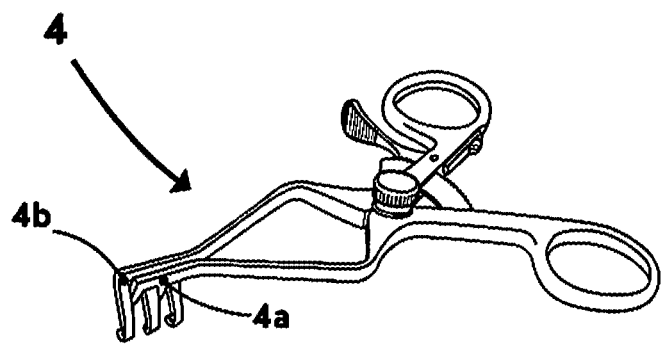
FIGS. 4A and 4B illustrate a prior art soft tissue retractor with interdigitated prongs, shown in open and closed positions, respectively.
Figure 4A:
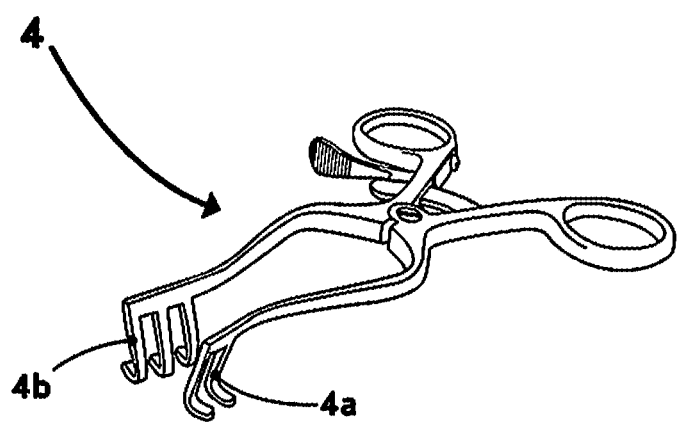

FIG. 3 illustrates another lamina spreader. The spreader 3 has "1×2" inter-digitated tips. The distractor has a swan neck "bayonet" shaft and blunt tips. The "paddle" sides of the interdigitated instrument 3 incorporate widely spaced prongs 3a, 3b which are straight with minimal serrations. The prongs of one side of the instrument 3 sit alongside or pass through the prongs of the other side of the instrument. Instead of having one plane where the two sides meet as in the small bone spreader of FIG. 2, each prong crosses this plane. This is also shown in the prior art retractor 4 of FIGS. 4A, 4B where the prongs 4 spread when the handles are squeezed together, and allowing for a lower profile The interlacing of these prongs 4a, 4b provides a low profile, and allows the two sides of the distracting paddles to occupy, essentially, the "same space." The prongs have a slight serration.

The bone distractors (retractors) of the present invention have numerous advantages over the prior art. Various embodiments of the bone distractors of the present invention are disclosed which provide a smooth outside surface/profile for entry and is openable so the serrated prongs pass the medial point for the serrations to transition to an outside surface. In the closed position, the serrated portion of each prong is protected by its inward position with respect to the smooth surface of the other prong. Various prong tips to facilitate entry into the joint are also disclosed.

As used herein, the term "distal" denotes the region, section or portion further from the user and the term "proximal" denotes the region, section or portion closer to the user.

Turning initially to FIGS. 5A-8D, a first embodiment of the bone distractor of the present invention is illustrated and designated generally by reference numeral 10. The smooth narrow tip of the wedge shape combined with the low profile and substantial prong of the interdigitated design assures smooth entry into tight spaces and provides strong distracting paddles that aren't likely to bend under pressure. The prongs 12, 14 (also referred to herein as blades or jaws) of the distractor 10 effectively hold on to the sides of joint. The prongs are curved and behave differently whether open or closed.

Prong 12 has a non-serrated, e.g. smooth, convex side (surface) 16 and a serrated concave side (surface) 18 with serrations (recessed teeth) 19. Prong 14 has a non-serrated, e.g., smooth, convex side (surface) 20 and a serrated concave side (surface) 22 with serrations 24. The prongs 12 and 14 extend transverse to a longitudinal axis of the arms of the bone distractor 10, and the serrations 19 and 24 extend along the length of the prongs 12 and 14, respectively, in a row extending transverse to the longitudinal axis of the arms of the bone distractor. The size and number of teeth can vary from that shown provided they provide a sufficient gripping force as described herein. The side opposing the serrated side can be smooth, non-serrated or otherwise have a surface less serrated than the serrated surface (portion) to facilitate insertion (and removal) by reducing frictional or more aggressive engagement with the bone surfaces.

Figure 5A:
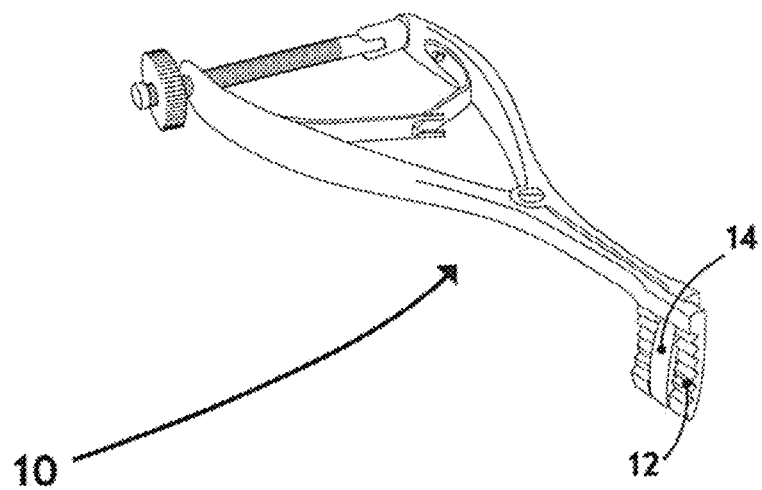
FIG. 5A is a perspective view of one embodiment of the distractor of the present invention.
Figure 5B:
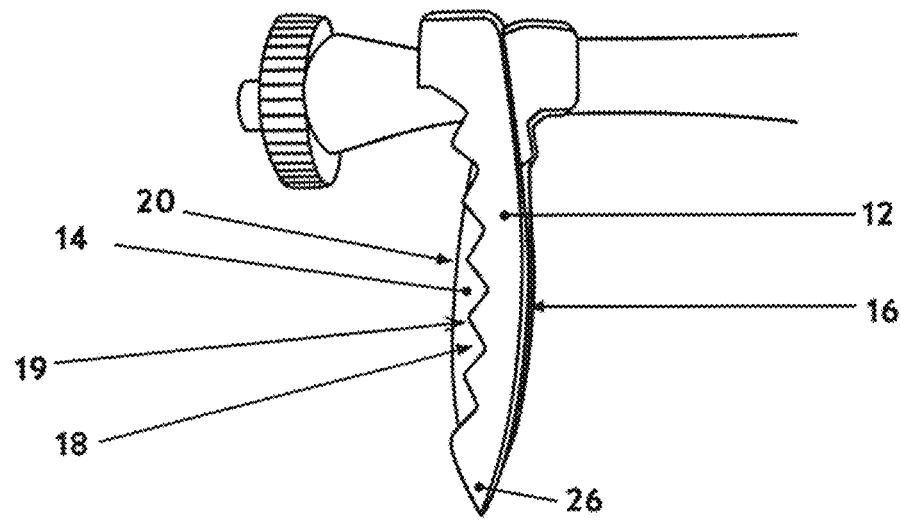
FIG. 5B is a front view of the distractor of FIG. 5A with the prongs of the interdigitated structure in the closed position.

The prongs 12, 14 of the distractor 10 in the closed position of FIG. 5B, provide two bowed halves, and their wedge shaped tips 26, 28, interdigitate and form the shape of a spear or a leaf as shown in FIG. 5B. Prong 12 can include two spaced apart serrated surfaces to provide a space 29 (FIG. 5E) to interdigitate with prong 14 to provide the spear or leaf shape. This shape provides smooth entry into the tight joint. In this closed position, the serrated convex sides are recessed behind (within) the smooth spear-shaped perimeter. This is best shown in FIGS. 5B and 5D where serrations 19 do not extend beyond side 20 of prong 14 and serrations 24 do not extend beyond side 16 of prong 12. (The serrations 24 are hidden in FIGS. 5B and 5D by the prong 12). Stated another way:

1) in the closed or insertion position, a) the serrated side 18 of the first prong 12 is positioned inwardly of the smooth side 20 of the second prong 14 so it is shielded from contact with the bone during insertion into the joint; and b) the serrated side 22 of the second prong 12 is positioned inwardly of the smooth side 16 of the first prong 12 so it is shielded from contact with the bone during insertion into the joint; and 2) in the open or in use position, a) the serrated side 18 of the first prong 12 is positioned outwardly of the smooth side 20 of the second prong 14 so it is in contact with the bone to distract the bone; and b) the serrated side 22 of the second prong 14 is positioned outwardly of the smooth side 16 of the first prong 14 so it is in contact with the bone to distract the bone.

Such movement of the prongs between the shielded and exposed positions is discussed below. Note the side of the prong opposite to the serrated side is described as smooth or non-serrated. It should be appreciated that the side does not need to be completely smooth or completely non-serrated as long as it provides improved surfaces for ease of insertion/ entry compared to the serrated sides which are shielded from contact, thus also referred to herein as having a "smoother" surface.

Figure 9G:
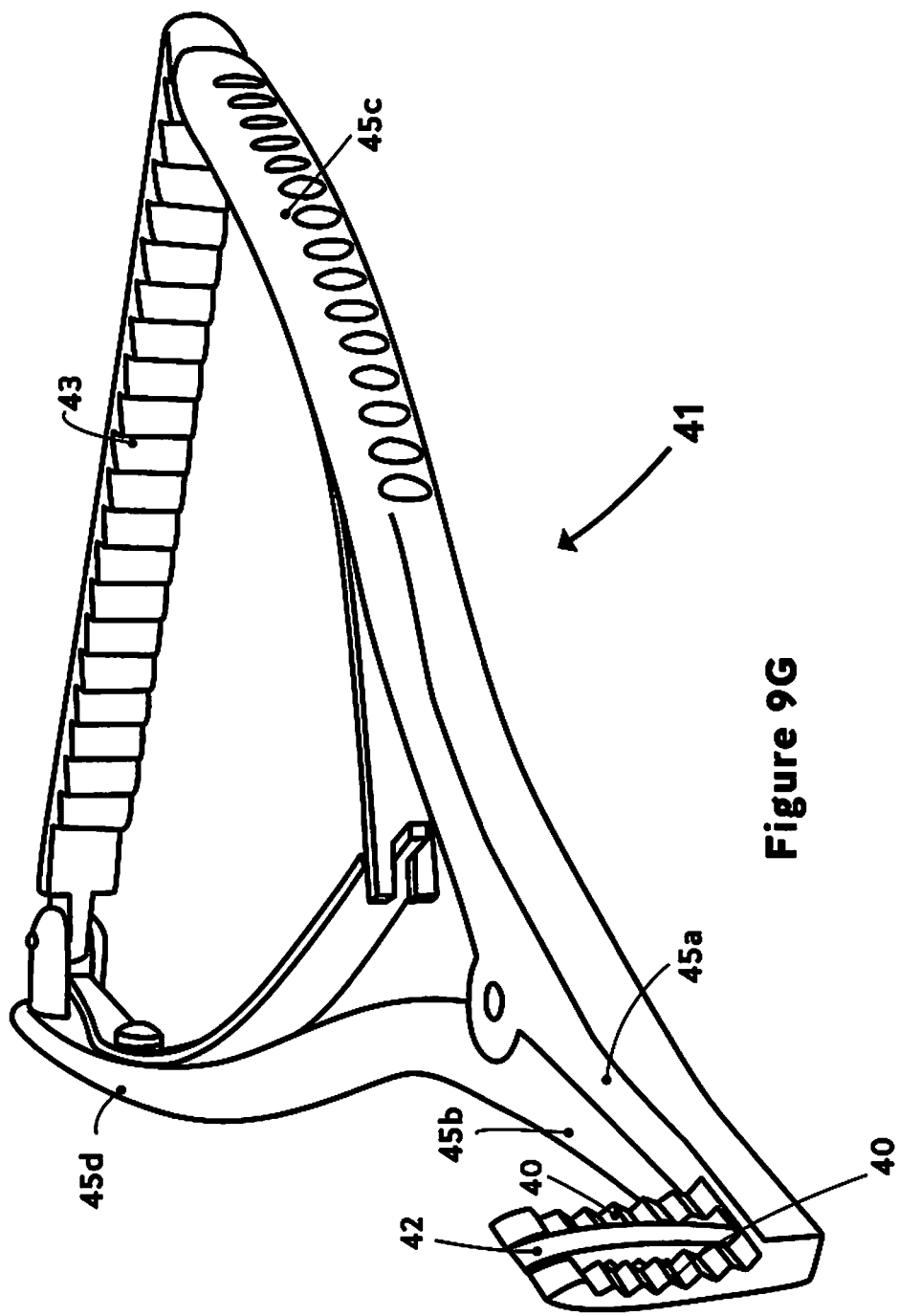
Figure 9H:
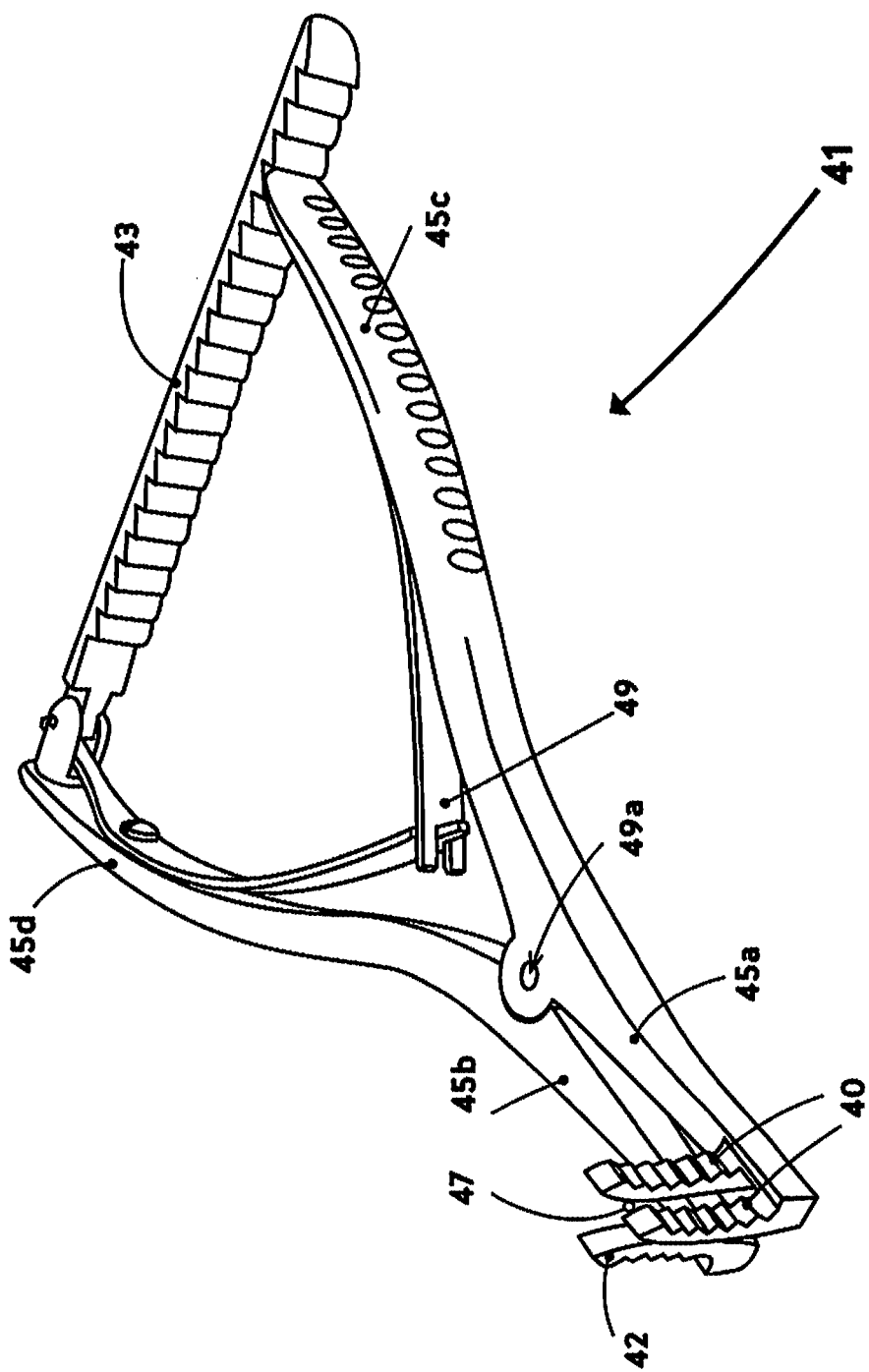
Figure 9I:
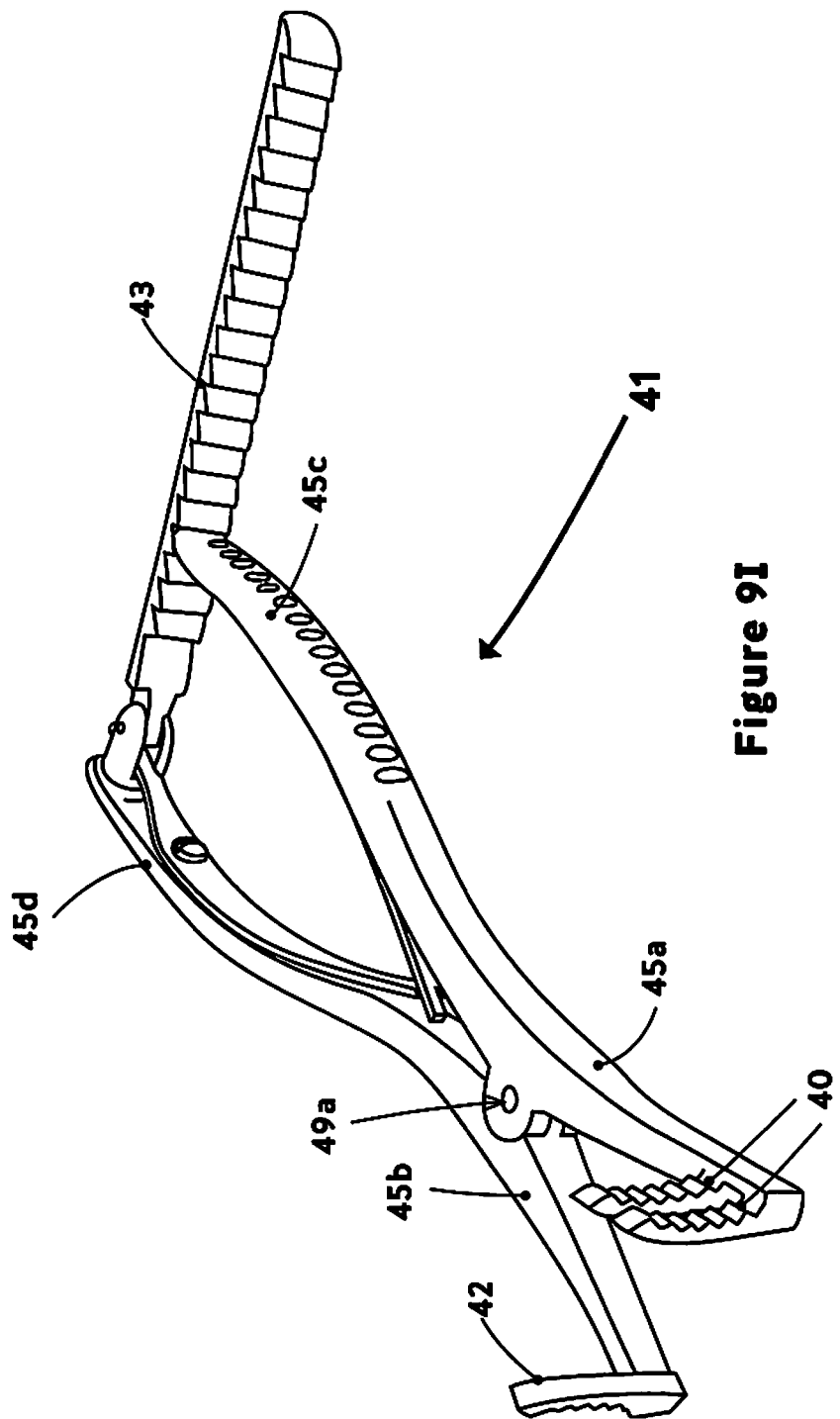

FIGS. 9A-9L illustrate an alternate embodiment of the distractor of the present invention with FIGS. 9A-9F showing the prongs (blades) in various positions and FIGS. 9G-9I showing the entire distractor, designated generally by reference numeral 41, in a closed, partially opened and almost fully opened position. In this embodiment, the prongs 40, 42 each have a convex side 44, 46 respectively which is more curved than sides 16 and 20 of prongs 12, 14 of FIGS. 5A-5D which are "straighter." The convex sides can alternatively be straighter (linear) or more curved than shown in the Figures. Note also the concavity and convexity of the sides of the various prongs disclosed herein can refer to the entire side or a portion of the side being convex or concave.

Figure 9J:
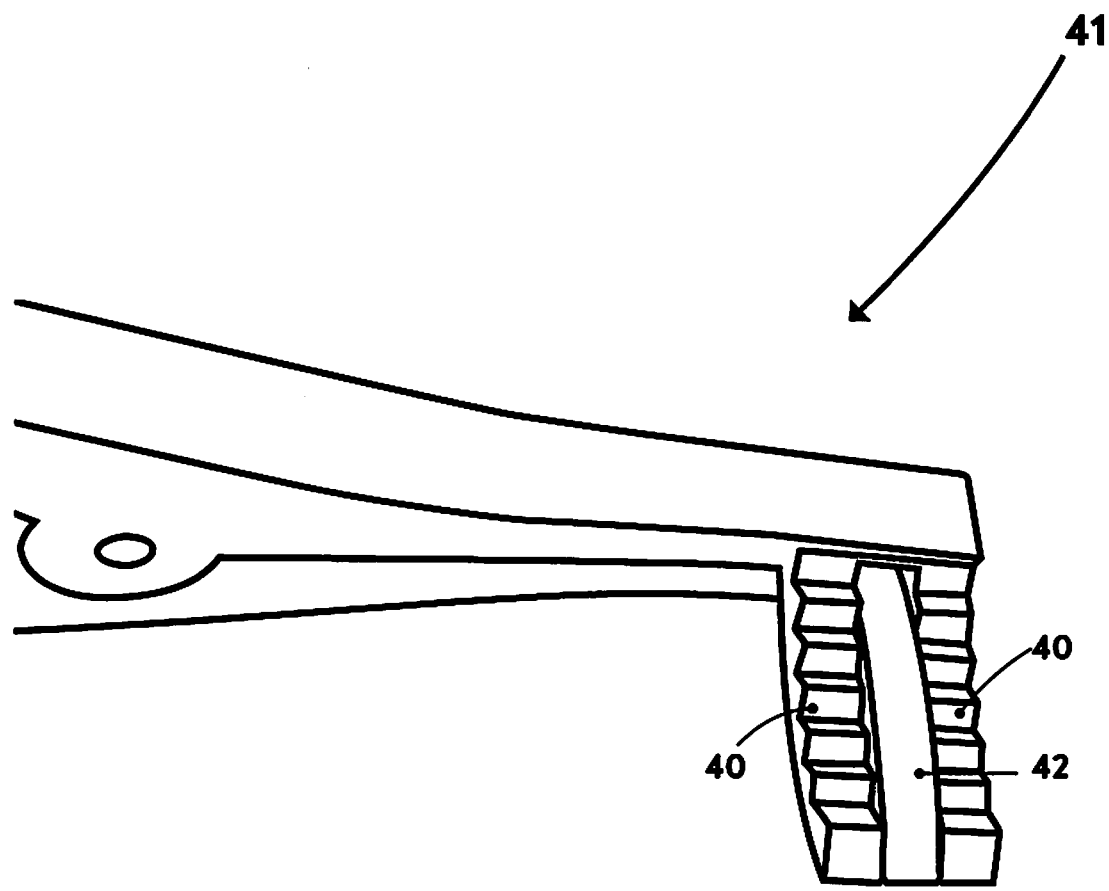
Figure 9K:
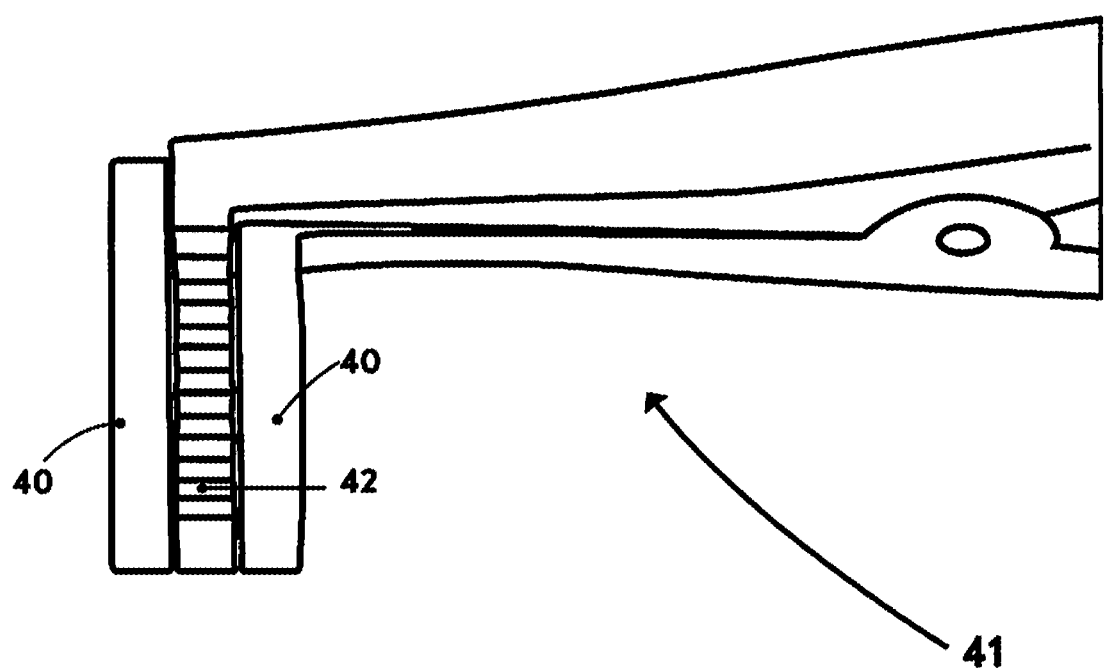
Figure 9L:
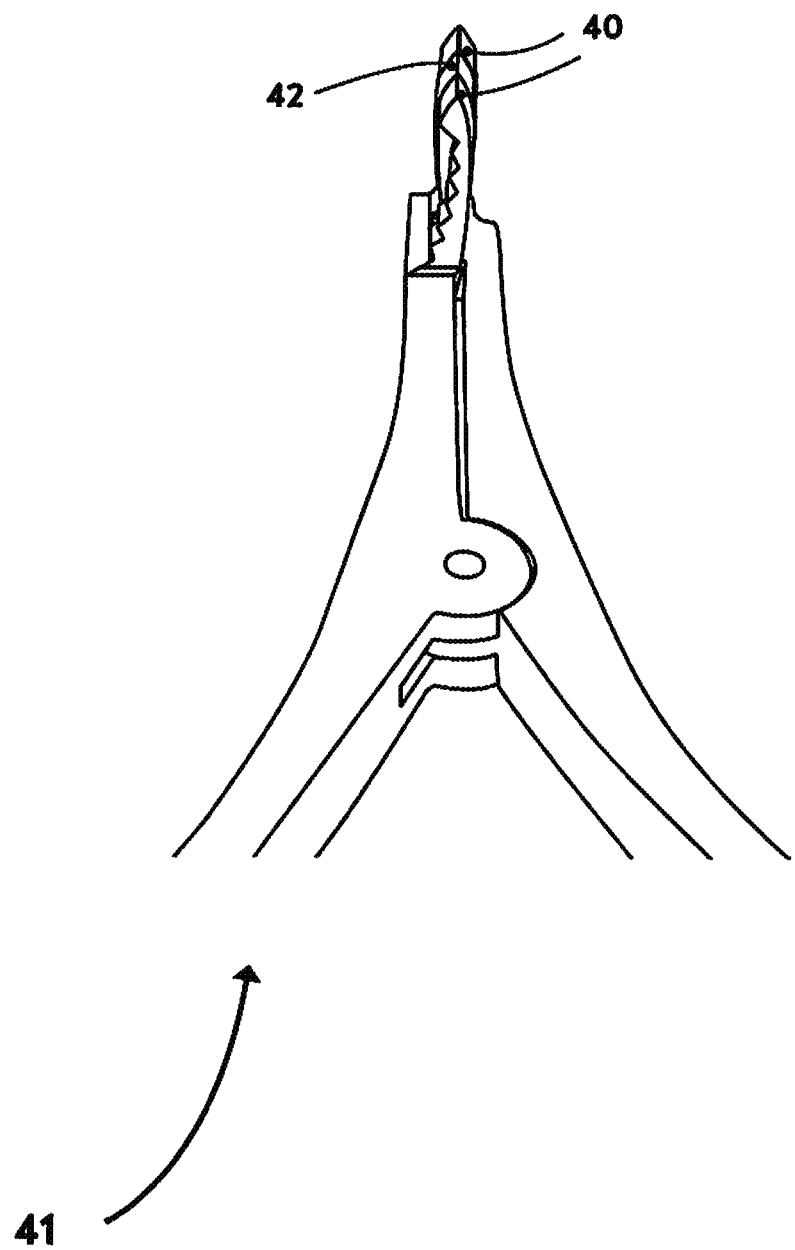
Figure 10:
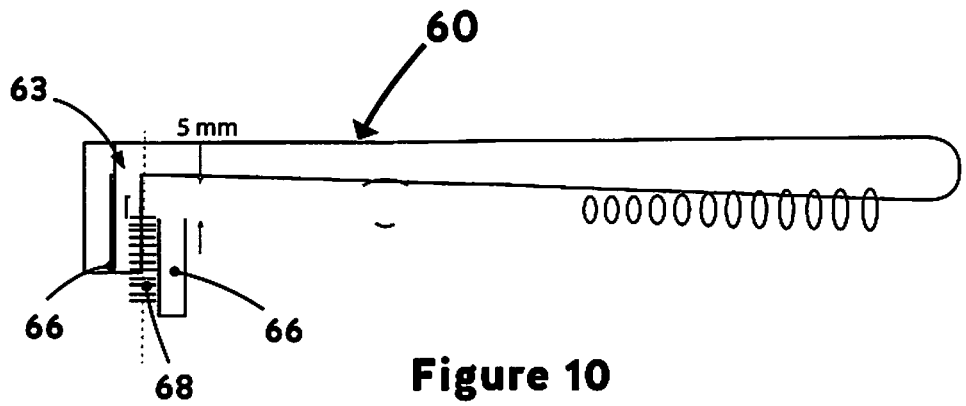
FIG. 10 is a side view of the distractor of FIG. 5A.

Prongs 40, 42, like prongs 12, 14, have recessed teeth or serrations 48, 50, respectively, on the concave side opposite the convex side formed in a row extending transversely to the arm of the distractor 41. In all other respects, the prongs of FIGS. 9A-9B, and the distractor which they are part of, and its function, are identical to prongs 12, 14 of distractor 10. FIGS. 9C, 9J and 9K illustrate the prongs 40, 42 in the closed position (protecting the serrated edges), FIG. 9E illustrates the prongs 40, 42 in transition from the closed position toward the open position as the prongs pass the medial point so the serrations become the outer surface. FIGS. 9B and 9I illustrate the prongs 40, 42 in the more open position for bone distraction. Note the transition position of FIGS. 9E and 9F provides the narrowest position (profile), and in the closed position of FIGS. 9C, 9D and 9L, the smooth wedge shape profile is provided. The interdigitation of the prongs 40, 42 is shown in FIGS. 9J and 9K with prong 42 positioned in the space 47 between the spaced apart pair of prong portions 40 which as illustrated has a serrated surface facing the opposite direction of the serrated surfaces of the other prong 40. That is, prong 40 has two spaced apart serrated surfaces/sides (with opposing smooth surfaces/ sides) with a space therebetween to receive a prong 42.

FIGS. 9G-9H illustrate the distractor 41 having a ratchet lock to maintain the prongs 40, 42 in the selected position. Ratchet lock 43 provides quick one-handed distraction for maintaining the arms 45a, 45b, and thus the prongs 40, 42, of distractor 41 in a closed position as the pawl engages the teeth. As shown, in FIG. 9G the prongs 40, 42 are in the closed position with the proximal portion 45c of arm 45a engaged with an end of the teeth furthest from proximal portion 45d of arm 45b (the proximal portion is 45c, 45d of arms 45a 45b are fully spread); in FIG. 9H the prongs 40, 42 are open as the proximal portions 45c, 45d of arms 45a, 45b are partially spread (or partially closed) with the proximal portion 45c of arm 45a engaged with the rack closer to the center; and in FIG. 9I the prongs 40, 42 are more open as the proximal portions 45c, 45d of arms 45a, 45b are even less spread (further closed) with the proximal portion 45c of arm 45a engaged with the rack closer to the opposing end from the engagement of FIG. 9G (closer to proximal portion 45d of arm 45b). Thus, in use, applying an inward force to portions 45c, 45d opens distal portions of the arms 45a, 45b (pivoting about hinge 49a) and thus opens the prongs 40, 42. A spring 49 can be provided to provide a biasing force to the arms 45a, 45b which needs to be overcome to move the arms 45a, 45b. Note the distractors of the other embodiments disclosed herein can have the arm and ratchet configuration and function as described herein for distractor 41.

Figure 22A:
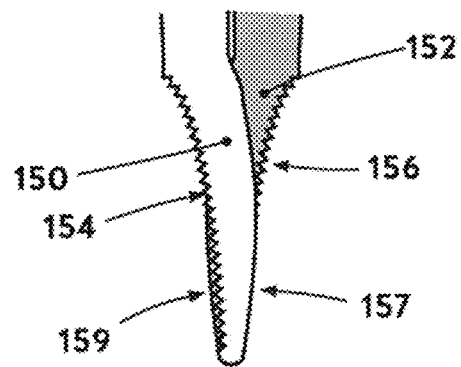
FIGS. 22A and 22B are front views of another alternate embodiment of the prongs of the present invention.
Figure 22B:
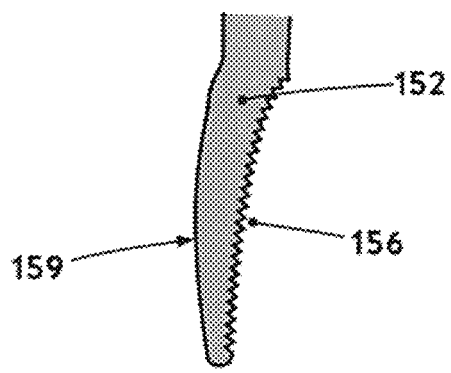

FIGS. 22A and 22B disclose another alternative configuration of prongs of the present invention having a convex side wherein prongs 150, 152 have serrations 154, 156 on a concave side (surface) and a convex smoother bowed side 157, 159 on the opposing side (surface). In all other respects, the prongs of FIGS. 22A-22B, and the distractor which they are part of, and its function, are identical to prongs 12, 14 of distractor 10. Thus, the serrations 154, 156 are shielded during insertion and moved beyond the smooth sides of the other prong to contact and distract the bone.

Figure 5C:
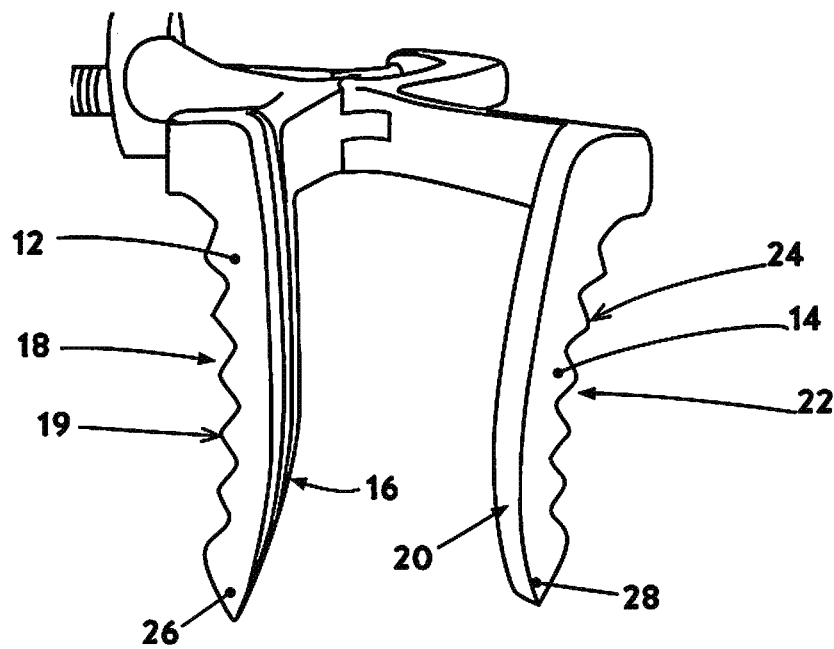
FIG. 5C is a front view of the distractor of FIG. 5A with the prongs of the interdigitated structure in the open position.
Figure 5D:
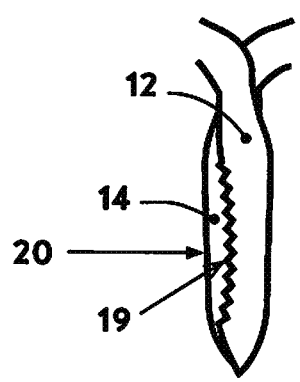
FIGS. 5D and 5E are front and side views of the prongs of the distractor of FIG. 5A.
Figure 5E:
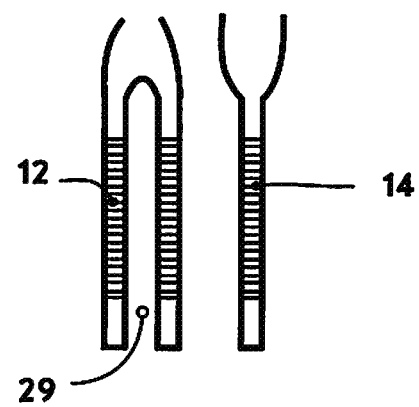

Turning back to distractor 10, when the distractor 10 opens from the position of FIG. 5B to the position of FIG. 5C, the prongs 12, 14 pass the medial plane and what was inside, is now outside and what was outside is now inside. This crossover immediately turns the serrated concave "inside" surfaces (sides) 18 and 22 (which were protected (shielded) by the other prong so the serrated surface was not in contact with the bone during insertion) into serrated outside surfaces. The now outer serrated concave surfaces grip securely to the inner surfaces of the joint. The distractor 10 can now effectively engage the joint space, distract the joint and stay in place. The concave surfaces 18, 22 also add the extra benefit of having curving distal ends which in certain instances can reduce the chance of the instrument "popping out." Despite the excellent grip, removal is as easy going in as it is coming out, so long as the instrument is returned to the closed position, i.e., moving the prongs 12, 14 to the position of FIG. 5B, so the serrated sides 18, 22 are moved inwardly of the smooth surfaces 16, 20, respectively, of the opposing prong as described above. The prongs 40, 42 as well as the prongs of the other embodiments disclosed herein function in this same crossover manner for insertion, distraction and removal.

Figure 12A:
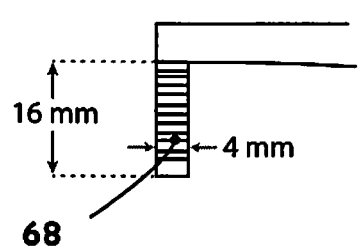
FIG. 12A is close up view of one embodiment of a prong of a distractor of the present invention and FIG. 12B is a side view of the two prongs of the other arm of the distractor.
Figure 12B:
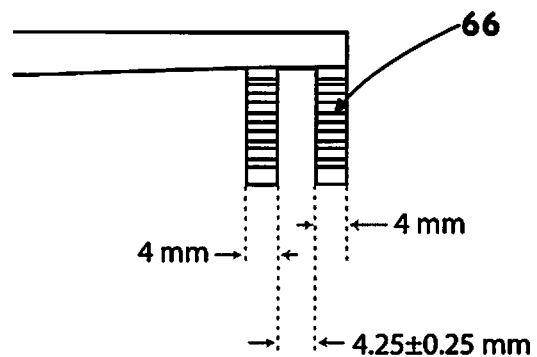
Figure 12C:
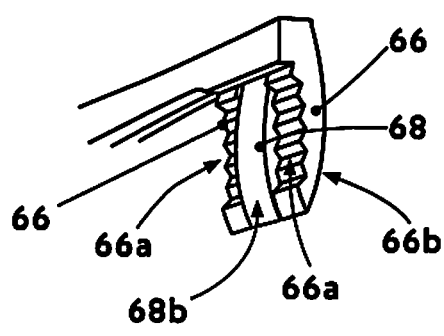
FIGS. 12C and 12D are perspective views of the interdigitated prongs of FIGS. 12A and 12B from opposite sides.
Figure 12D:
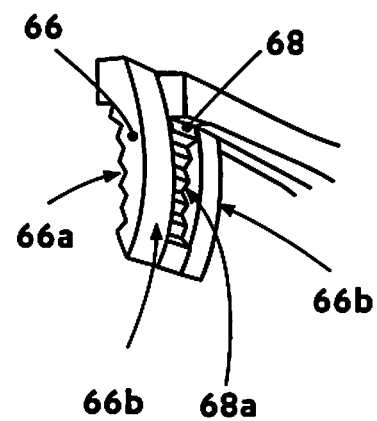

The prongs 66, 68 shown in FIGS. 10 and 12A-12D, illustrate dimensions of one embodiment of the prongs (blades), however, other dimensions are also contemplated. The shape of the prongs 66, 68 are similar to the shape of the prongs 40, 42 of FIG. 9A. In this embodiment, one or both of the arms taper distally at region 63 to a minimum thickness of 5 mm, although other dimensions are also contemplated. (see e.g., a thickness of 3 mm in FIG. 13). The width is shown by way of example as 4 mm and a length of 16 mm, although other dimensions are also contemplated. The other prongs disclosed herein can also have these or other dimensions. FIGS. 12C and 12D are perspective side views of the blades of FIGS. 12A and 12B shown interdigitated and further showing the curvature and wedge shape. As can be appreciated, in this closed position the serrated sides 68a of prong 68 are recessed with respect to the smoother outer surface 66b of the other prong 66 and serrated side 66a of prong 66 is recessed with respect to the smoother outer surface 68b of the other prong 68 in the same manner as prongs 12 and 14 of FIG. 5B. Prongs 66, 68 function in the same way as prongs 12 and 14 of distractor 10.

The depth and width of the blades (prongs) of the various embodiments disclosed herein can vary from those illustrated. Additionally, the shape and angle onto which the blades are mounted on the frame can be 90 degrees as shown or alternatively mounted at angles other than 90 degrees with respect to the arms. Note the serrations are shown as horizontal, but alternatively cross-serrations or other arrangements of the serrations can be utilized. As noted above, the side opposite the serrated side is configured to be "less insertion impeding" or "less interfering" which in preferred embodiments is smooth, The use of the distractor of the present invention can best be understood with reference to FIGS. 6A-8D. FIGS. 6A-6D show the steps of insertion of the distractor 10 (with the prongs in the closed position); FIGS. 7A-7D show the steps of distraction of the distractor 10 and FIGS. 8A-8D show the steps of removal of the distractor 10. The other embodiments of the distractors disclosed herein, e.g., the various prong configurations, are utilized in the same manner as FIGS. 6A-8D, That is, for convenience, the use of the distractor 10 is illustrated and described, it being understood that the use of distractor 10 as shown and described is fully applicable to the use of the other distractors disclosed herein.

Figure 6D:
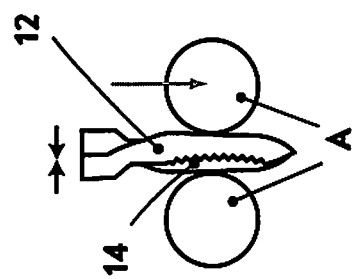
FIGS. 6A-6D illustrate the steps of insertion of the distractor of FIG. 5A.
Figure 6C:
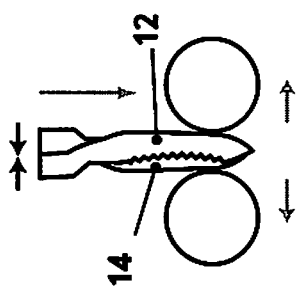
Figure 6B:
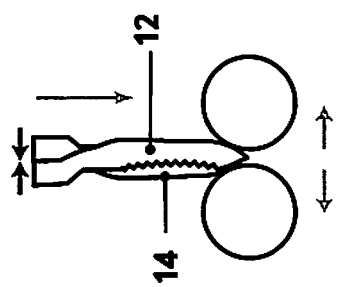
Figure 6A:
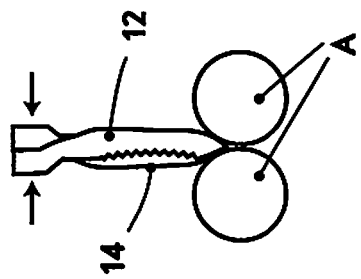

As shown in FIG. 6A, the prongs are in the closed position. As explained above, when in the closed position, the teeth (serrated surface) are protected by the smoother (or smooth) backside of the other prong (jaw), allowing the prongs 10, 12 to slide into the position between bones A without the teeth (serrations) interfering as shown in FIGS. 6C and 6D.

Figures 7A, 7B, 7C, 7D:
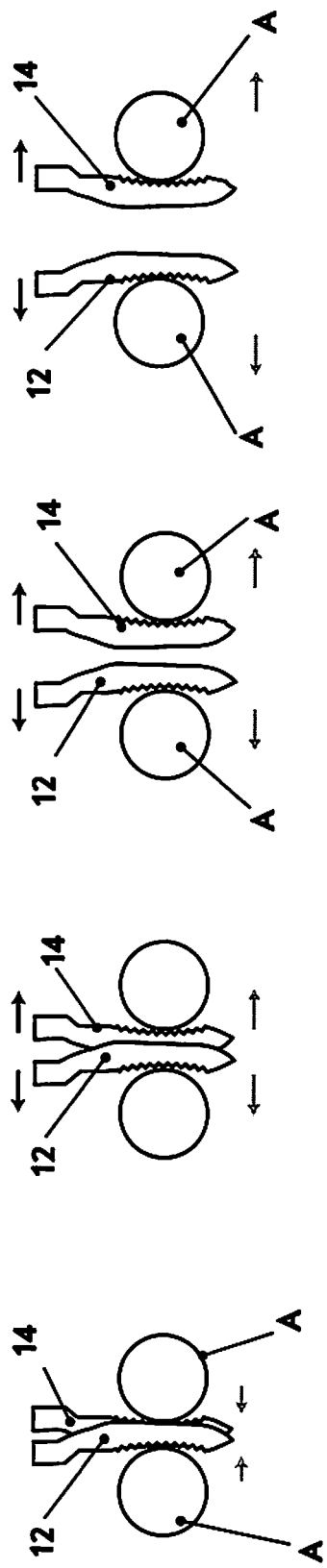
FIGS. 7A-7D illustrate the steps of distraction of the distractor of FIG. 5A.

Once in position, the distractor 10 can now distract. As this occurs, it passes through its narrowest position when it starts to expose the teeth. This action exposes the teeth 19 and 24 of prongs 10, 12 as shown in FIG. 7B. Once the teeth are engaged, the prongs can hold onto the bone and won't slip out as it distracts as shown in FIGS. 7C and 7D.

Figure 8D:
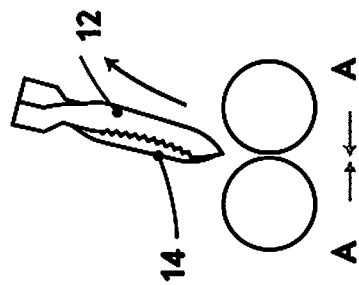
FIGS. 8A-8D illustrate the steps of removal of the distractor of FIG. 5A.
Figure 8C:
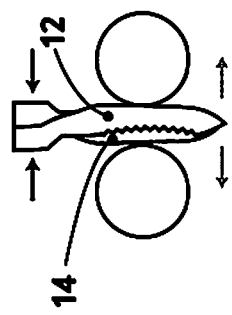
Figure 8B:
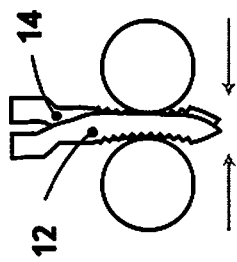
Figure 8A:
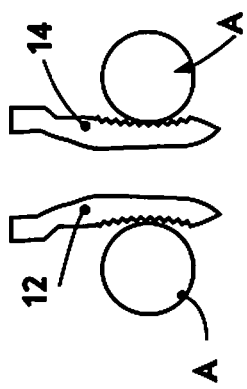

For removal, the tension (ratchet) on the distractor 10 is released and it moves to its narrowest position as shown in FIG. 8B. At this point, the serrated sides (surfaces) are still engaged with the bone A. The retaining ratchet is released and the distractor is moved to the fully closed position for smooth easy removal as the sides become smooth again as the serrated surfaces are moved inwardly of the smooth surfaces so the smooth surfaces become the outer exposed surfaces rather than the serrated surfaces. This is shown in FIG. 8C. With the serrated surfaces out of contact with the bone and the smooth surfaces in contact with the bone, the distractor can slide out unencumbered as shown in FIG. 8D.

Figure 23A:
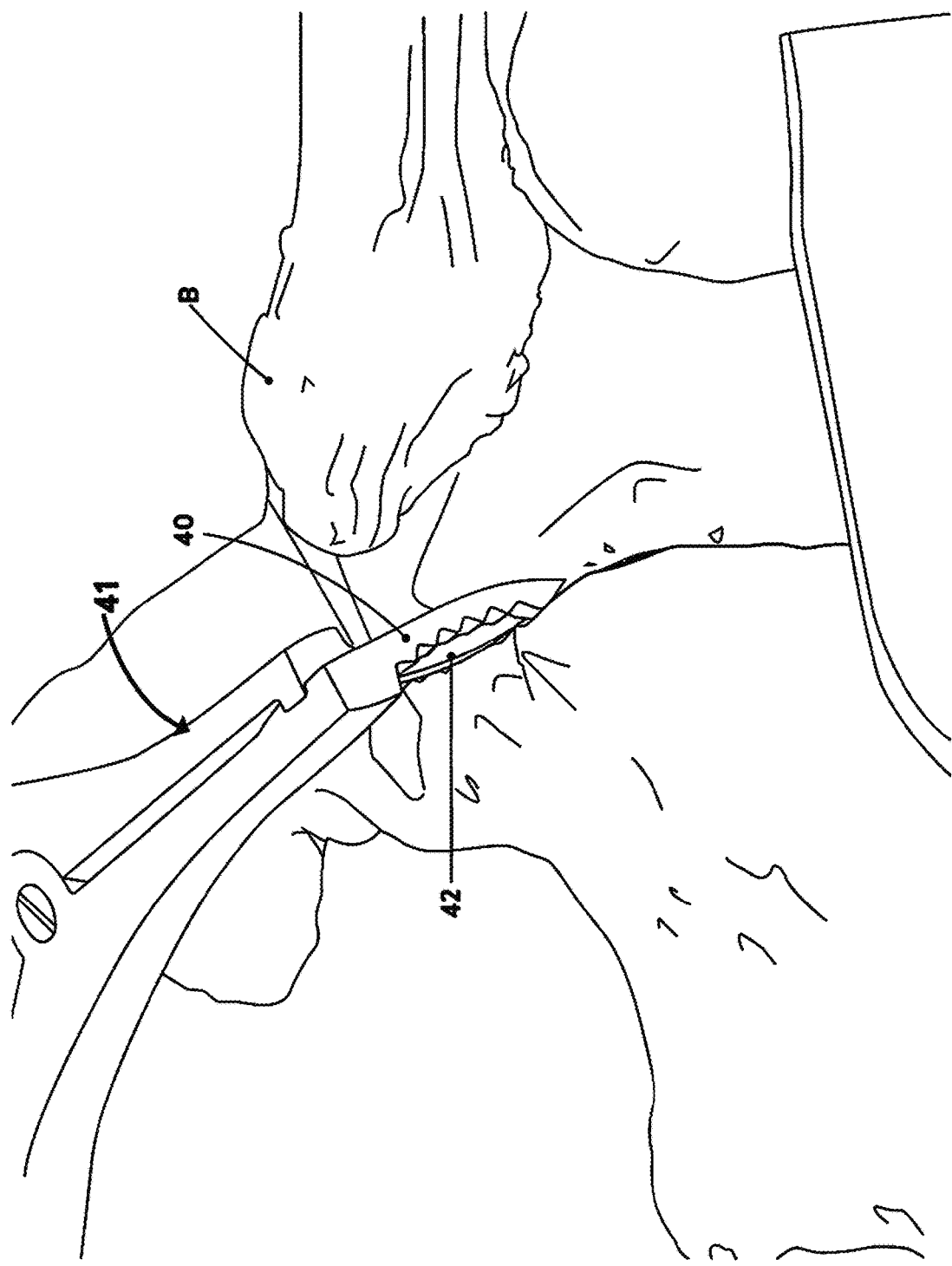
FIG. 23A is a perspective view of the distractor of FIG. 9G shown being inserted into a bone space.
Figure 23B:
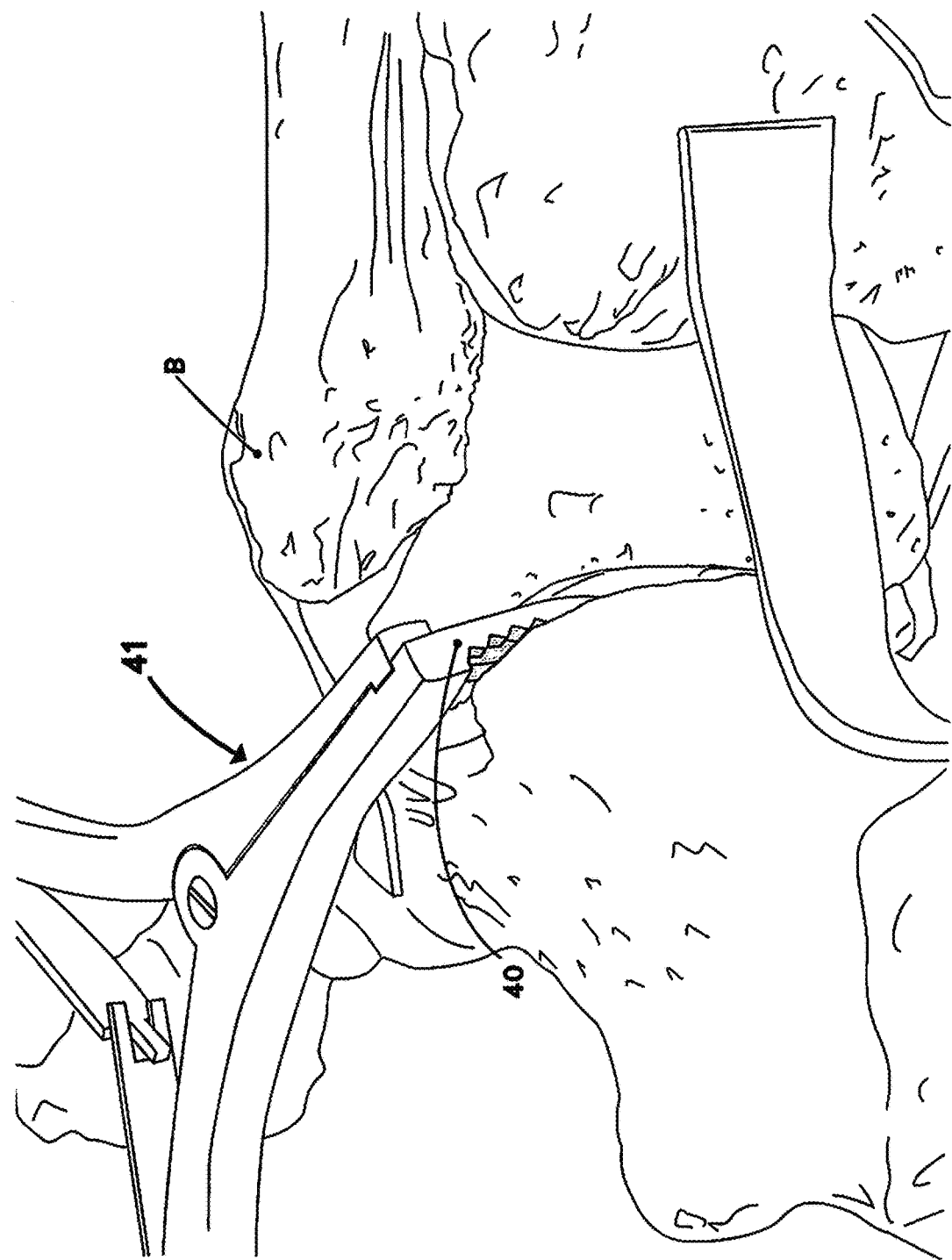
FIG. 23B is a perspective view of the distractor of FIG. 9G shown fully inserted into the bone space.
Figure 23C:
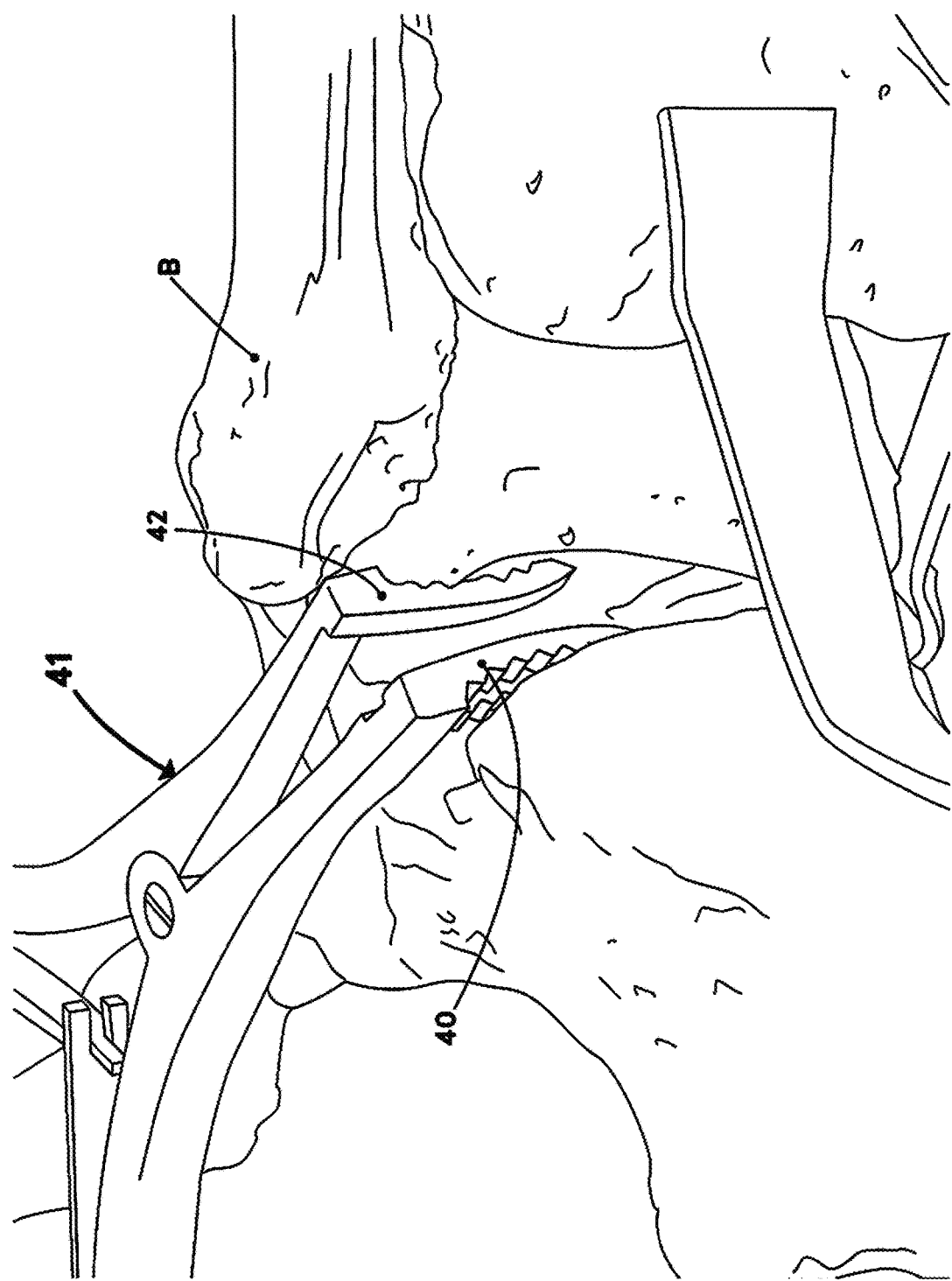
FIG. 23C is a perspective view of the distractor of FIG. 9G shown being opened within the bone space to distract the bone.

FIGS. 23A, 23B and 23C illustrate the distractor in use in the body to distract bone. The use of the distractor in bone is illustrated using distractor 41, however, the other distractors disclosed herein, e.g., the various prong configurations, are utilized in the same manner as shown in FIGS. 23A-23C. In FIG. 23A, the distractor 41 is inserted into the space in the bone with the prongs 40 and 42 in the closed position of FIGS. 9C and 9G to shield the serrated surfaces. FIG. 23B shows full insertion into the bone space. The proximal portion 45c of arm 45a is moved toward the proximal portion 45d of arm 45b as described above in conjunction with FIG. 9G-9I to spread the prongs 40, 42 apart to distract the bone B as shown in FIG. 23C to expose the serrated surfaces for gripping the bone surface to secure the distractor 41. To remove the distractor 41 from the bone space, proximal portion 45c of arm 45a is moved away the proximal portion 45d of arm 45b, thereby moving the prong 40 back toward prong 42 to the closed interdigitated and shielded position of the serrated surfaces.

It should be appreciated that to open and close the prongs of the various embodiments disclosed herein, either one arm can be movable away from and toward a fixed (stationary) arm or both arms can move away from and toward each other.

Figure 11A:
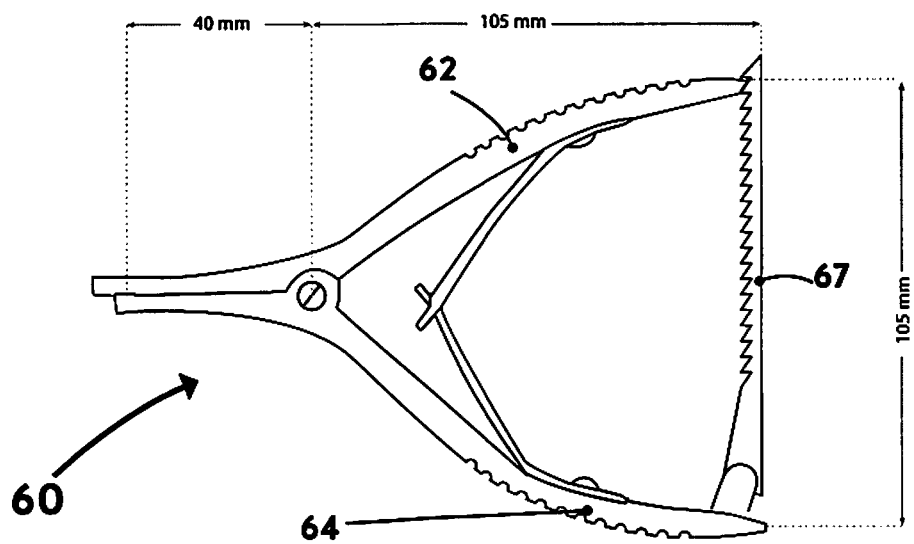
FIGS. 11A and 11B are top and front views of an alternate embodiment of the distractor of the present invention.
Figure 11B:
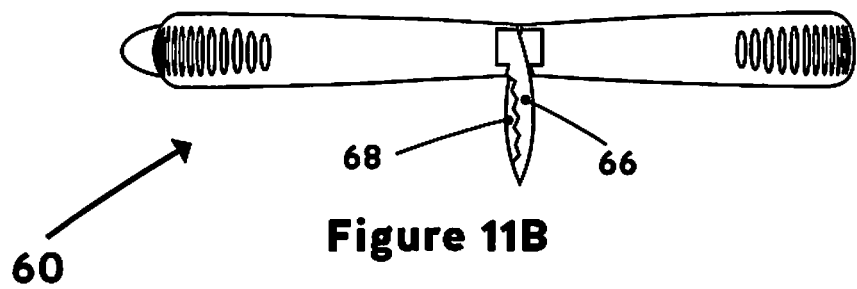

The distractors of the present invention can include a ratchet, notch or a spin lock to maintain it in the closed position. Other types of locks are also contemplated to maintain the prongs in the closed position. FIG. 11A illustrates by way of example a ratchet lock 67 similar to the distractor 41 of FIG. 9G providing quick one-handed distraction for maintaining the arms 62, 64, and thus the prongs, of distractor 60 in the desired select position as the pawl engages the teeth of the rack 67. The proximal portions of the arms 62, 64 are spring biased to the open position.

Figure 13:
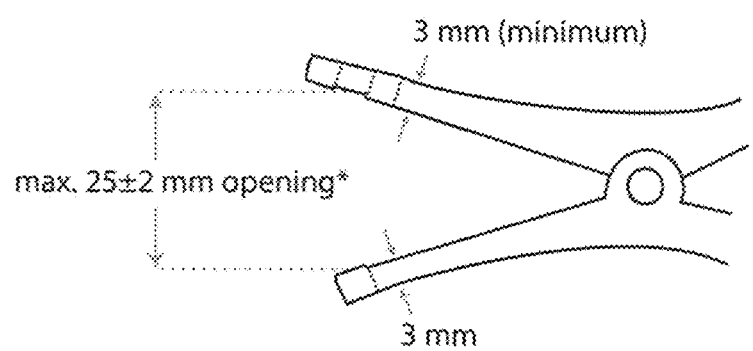
FIG. 13 is a side view of one embodiment of the blades of the distractor of the present invention shown in the open position to illustrate the gap between the blades.

FIG. 13 illustrates one embodiment of a gap between the prongs, e.g., showing by way of example a maximum 25 mm opening. Note in the open position, the indicated maximum opening is measured from the median line of the blades. It should be appreciated that this dimension as well as other dimensions provided in the drawings of this application and/or discussed herein are provided by way of example as other dimensions are also contemplated.

Figure 14B:
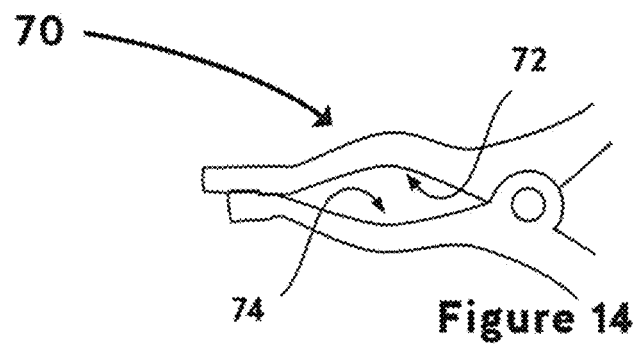
FIGS. 14A and 14B are side views of an alternate embodiment of the distractor of the present invention having an increased gap between the blades, the distractor shown in the open and closed positions. respectively.
Figure 14A:
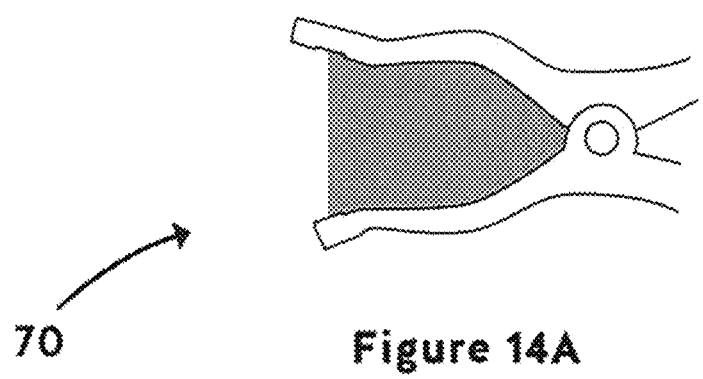

In the embodiment of FIGS. 14A and 14B, the distractor 70 has a bowed design which in certain instances can provide greater access to the distracted area as the bowed arms would create a larger U-shape access area between the arms rather than the smaller V-shape created by the straight arms. Note as compared to FIG. 13, the bowed or recessed areas 72, 74 create a larger gap, shown schematically as the darkened region. The distractor 70 is shown in the open and closed positions. In all other respects, distractor 70 is the same as distractor 10. This bowed design can be used with any of the distractors disclosed herein.

FIGS. 15A-21B illustrate alternate embodiments of the interdigitating prongs of the present invention. The embodiments of FIGS. 15A-21B illustrate various configurations of the prongs to achieve the profile for insertion and to shield the serrations during insertion (when in the closed position) and transition the serrations from inner surfaces (when closed) to outer surfaces upon opening the distractor as explained in detail above with respect to the other embodiments.

Figure 15A:
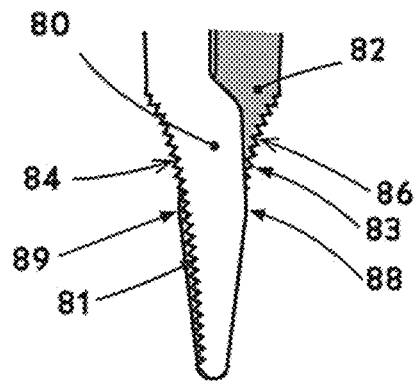
FIGS. 15A and 15B are front views of another alternate embodiment of the prongs of the present invention.
Figure 15B:
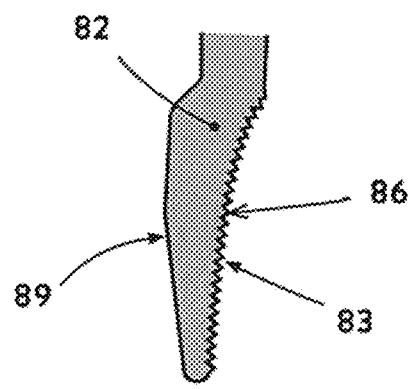

In FIGS. 15A and 15B, the prongs 80, 82 have an increased thickness compared to the embodiment of FIG. 9A. A plurality of teeth or serrations 84, 86 are provided on the concave sides 81, 83, respectively, of the interdigitating prongs 80, 82, respectively. The convex smoother side of each prong 80, 82, has a respective bend 88 and bend 89 or bowed shape (to form a taper for insertion).

Figure 16A:
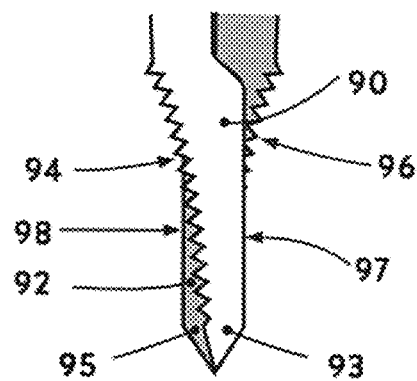
FIGS. 16A and 16B are front views of another alternate embodiment of the prongs of the present invention.
Figure 16B:
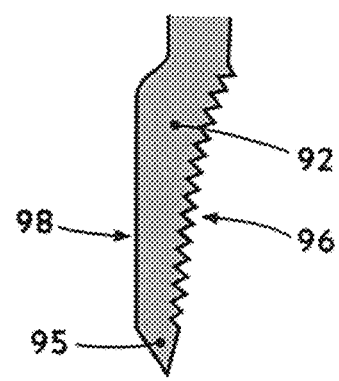
Figure 17A:
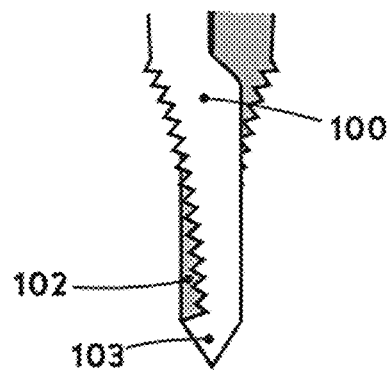
FIGS. 17A and 17B are front views of another alternate embodiment of the prongs of the present invention.
Figure 17B:
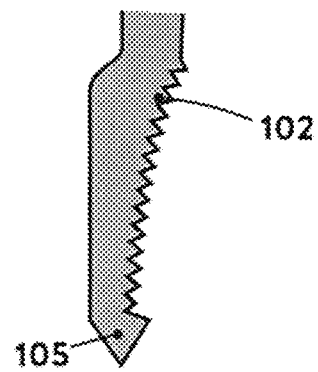

In FIGS. 16A and 16B, the interdigitating prongs 90, 92 have an increased thickness as in FIG. 15A but have a half wedge tip 93, 95, respectively, that line up to form a more solid wedge when in the closed position. In this half wedge design, the prong tip does not fully eclipse the wedge on the other prong in the closed position as shown. In this embodiment, the serrated sides (surfaces) 94, 96 and the opposing sides (surfaces) 97, 98 have a flatter (more linear) profile which could be fully linear or have a slight curve.

Figure 18A:
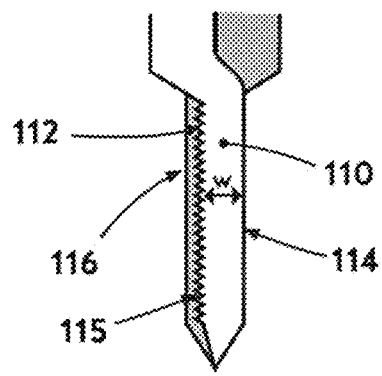
FIGS. 18A and 18B are front views of another alternate embodiment of the prongs of the present invention.
Figure 18B:
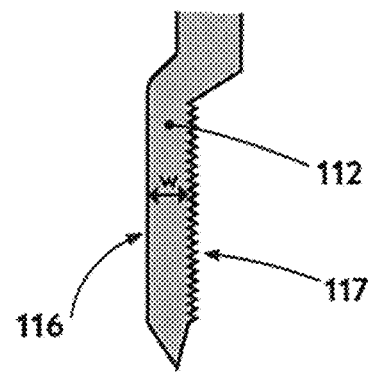
Figure 19A:
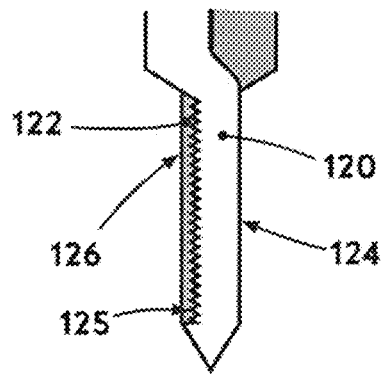
FIGS. 19A and 19B are front views of another alternate embodiment of the prongs of the present invention.
Figure 19B:
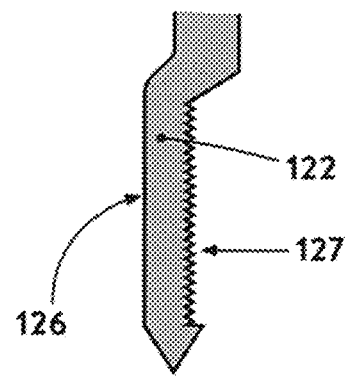

In FIGS. 18A and 18B, the prongs 110, 112 have serrated and smooth flat sides 115, 114, and 117, 116, respectively, and do not taper along their length so that the width w of the prongs 110, 112 remains constant along the length of the prong. Note prongs 110, 112 have a half wedge tip as in prongs 90, 92 of FIG. 16A but alternatively these flat (linear profile) sided prongs 110, 112 could have a full wedge tip such as the prongs 100, 102 of FIGS. 17A and 17B. The prongs 100, 102 differ from the prongs 90, 92 of FIG. 16A in that prongs 100, 102 have a full wedge tip 103, 105. The full wedge tips form a ledge/ridge at the entry point. The prongs 100, 102 have a straighter side opposite the side with serrations as in the embodiment of FIG. 16A. The prongs 120, 122 of the embodiment of FIGS. 19A and 19B have the full wedge tip like prongs 100, 102 of FIG. 17A, except the prongs 120, 122 have the serrated and smooth flat inner and outer edges 125, 124, 127, 126 and the constant width as in prongs 110, 112 of the embodiment of FIG. 18A.

Figure 20A:
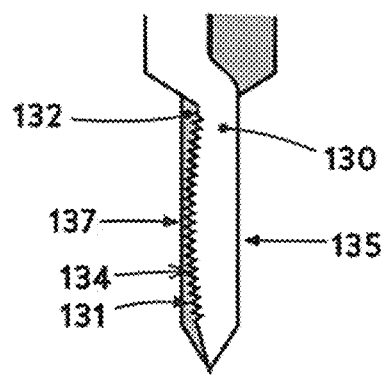
FIGS. 20A and 20B are front views of another alternate embodiment of the prongs of the present invention.
Figure 20B:
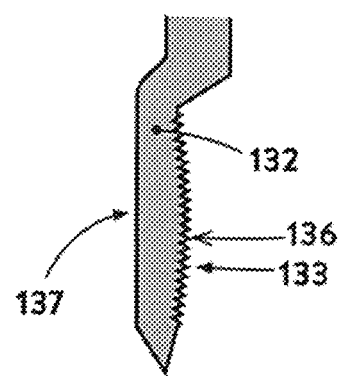
Figure 21A:
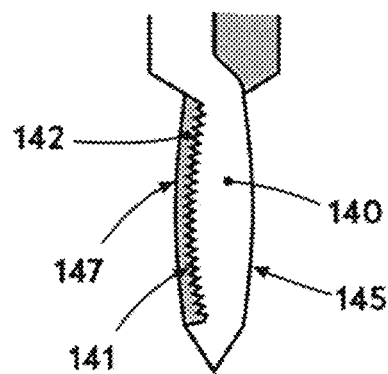
FIGS. 21A and 21B are front views of another alternate embodiment of the prongs of the present invention.
Figure 21B:
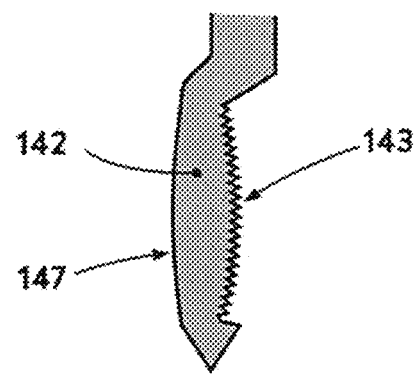

In the embodiment of FIGS. 20A and 20B, the prongs 130, 132 have a plurality of teeth or serrations 134, 136 on sides 131, 133, respectively. In this embodiment, instead of having a concavity or being flat as in the foregoing embodiments, the serrated sides 131, 133 are convex. As can be appreciated, even with this convexity, the prongs are configured and dimensioned so that the serrations 134, 136 are shielded (protected) by the smoother side 135, 137 of the other prong in the closed position as the serrations do not extend beyond the outer edge of the smoother surface 135, 137 of the opposing prong. The smoother sides 135, 137 can have a curve or be flat as in the aforedescribed embodiments. Note the prongs 130, 132 have the half wedge tip configuration as in FIG. 18A but alternatively could have the full wedge (arrow shape) of FIG. 19A. In FIGS. 21A and 21B, the prongs 140, 142 have the convex serrated sides 141, 143 as in FIG. 20A, and instead of the slight curve or flat smoother side of FIG. 20A, have a convex or bowed smooth side 145, 147. This outer convex shape in the closed position might be beneficial in uneven bone surfaces. The prongs 140, 142 have the full wedge tip like in prongs 90, 92 of FIG. 17A, but alternatively can have the half wedge tip configuration of FIG. 20A or, like the other prongs disclosed herein, can have a tip configuration other than full or half wedge shaped.

The distractors of the present invention provide a way to get a relatively narrow object to slide into a strong, tight, hard space and distract it without losing traction. They can be used in the small bones of the ankle or in other bones. The distractors could also have use in veterinary applications.

Although the apparatus and methods of the subject invention have been described with respect to preferred embodiments, those skilled in the art will readily appreciate that changes and modifications may be made thereto without departing from the spirit and scope of the present invention as defined by the appended claims.

What is claimed is:

1. A bone distractor comprising:
a first prong having a first side and an opposing second side, the first side having a serrated portion and the second side having a portion smoother than the serrated portion of the first side;
a second prong having a third side and an opposing fourth side, the third side having a serrated portion and the fourth side having a portion smoother than the serrated portion of the third side;
wherein in an insertion position of the bone distractor the first side is positioned inwardly of the fourth side and the third side is positioned inwardly of the second side so the smoother portions are in contact with bone during insertion and the serrated portions of the first side and of the second side are out of contact with bone during insertion; and
wherein during a use position of the bone distractor to distract bone the first side is moved outwardly of the fourth side and the third side is moved outwardly of the second side to place the serrated portions in contact with bone.

2. The bone distractor of claim 1, wherein in the insertion position, the first and second prongs interdigitate.

3. The bone distractor of claim 1, wherein the first prong has two serrated portions forming a space therebetween, and in the insertion position the second prong is positionable within the space.

4. The bone distractor of claim I, wherein the bone distractor has a longitudinal axis, and the serrated portions of the first and third sides comprise a series of teeth extending in a row transverse to the longitudinal axis.

5. The bone distractor of claim 2, wherein the interdigitated first and second prongs in the insertion position form a shape of a spear.

6. The bone distractor of claim 1, wherein the first and third sides are concave.

7. The bone distractor of claim 6, wherein the second and fourth sides are convex.

8. The bone distractor of claim 1, wherein the second and fourth sides are convex.

9. The bone distractor of claim 1, wherein the first and third sides are convex.

10. The bone distractor of claim 1, wherein the first and third sides have a linear profile.

11. The bone distractor of claim 1, wherein tips of the first and second prongs have a half wedge.

12. The bone distractor of claim 1, wherein the first and second prongs have a full wedge tip forming a ledge at an entry point.

13. A bone distractor comprising: a first prong extending from a first arm and a second prong extending from a second arm, the first and second prongs movable between open and closed positions, the first and second prongs each having a serrated side, wherein in the closed position for insertion into bone space, the serrated sides of the first and second prongs are configured to be out of engagement with the bone due to being shielded by the other prong and movement of the prongs to the open position moves the serrated sides of the first and second prongs into engagement with the bone.

14. The bone distractor of claim 13, wherein the first and second prongs each have a smoother side opposite the serrated side, and in the closed position the serrated side of the first prong is positioned inwardly of the smoother side of the second prong and the serrated side of the second prong is positioned inwardly of the smoother side of the first prong so that the serrated sides are configured to be kept out of contact with the bone for insertion.

15. The bone distractor of claim 14, wherein the smoother sides are convex.

16. The bone distractor of claim 14, wherein movement of the first and second prongs to the open position to distract the bone moves the serrated sides of the first and second prongs past a medial plane.

17. The bone distractor of claim 14, wherein in the closed position, the first and second prongs interdigitate.

\* \* \* \* \*